(12) United States Patent
Branch et al.

(10) Patent No.: US 7,513,869 B2
(45) Date of Patent: Apr. 7, 2009

(54) INSTRUMENTS AND METHODS FOR MINIMALLY INVASIVE TISSUE RETRACTION AND SURGERY

(75) Inventors: Charles L. Branch, Advance, NC (US); Eric C. Lange, Germantown, TN (US); Jonathan Dewey, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 501 days.

(21) Appl. No.: 10/792,358

(22) Filed: Mar. 3, 2004

(65) Prior Publication Data

US 2004/0176665 A1 Sep. 9, 2004

Related U.S. Application Data

(63) Continuation-in-part of application No. 10/180,658, filed on Jun. 26, 2002, now Pat. No. 6,945,933.

(51) Int. Cl.
*A61B 1/32* (2006.01)
(52) U.S. Cl. .................. 600/210; 600/214; 600/215; 600/233
(58) Field of Classification Search .............. 600/114, 600/232, 233, 210, 213, 214, 235, 215, 205, 600/201, 221, 224, 219, 206, 207, 208; 606/119, 606/197, 198, 96

See application file for complete search history.

(56) References Cited

U.S. PATENT DOCUMENTS

| | | | |
|---|---|---|---|
| 563,236 A | | 6/1896 | Penhall |
| 1,400,616 A | | 12/1921 | McCrory |
| 1,613,141 A | * | 1/1927 | Stein ........................... 600/232 |
| 2,661,735 A | | 12/1953 | Darden |
| 2,670,731 A | * | 3/1954 | Zoll et al. .................... 600/232 |
| 2,693,795 A | * | 11/1954 | Grieshaber .................. 600/213 |
| 3,054,398 A | | 9/1962 | Kobler |
| 3,747,592 A | | 7/1973 | Santos |
| 3,752,149 A | | 8/1973 | Ungar et al. |
| 3,788,318 A | | 1/1974 | Kim et al. |
| 3,965,890 A | | 6/1976 | Gauthier |
| 4,263,899 A | * | 4/1981 | Burgin ......................... 600/213 |
| 4,380,999 A | * | 4/1983 | Healy .......................... 600/228 |

(Continued)

FOREIGN PATENT DOCUMENTS

DE 87 04 901 U 7/1987

(Continued)

OTHER PUBLICATIONS

U.S. Appl. No. 10/720,656, filed Nov. 24, 2003, Frey et al.

*Primary Examiner*—Pedro Philogene
(74) *Attorney, Agent, or Firm*—Krieg DeVault LLP

(57) ABSTRACT

Methods and devices retract tissue for minimally invasive surgery in a patient. A retractor includes a working channel formed by a first portion and a second portion. The first and second portions are movable relative to one another from a first configuration for insertion that minimizes trauma to skin and tissue to an enlarged configuration after insertion to further retract skin and tissue in a minimally invasive manner. Instruments are engageable to the first and second portions and operable to move the first and second portions relative to one another.

44 Claims, 22 Drawing Sheets

U.S. PATENT DOCUMENTS

| | | | |
|---|---|---|---|
| 4,545,374 A | 10/1985 | Jacobson | |
| 4,616,635 A | 10/1986 | Caspar et al. | |
| 4,716,901 A | 1/1988 | Jackson et al. | |
| 4,747,394 A | 5/1988 | Watanabe | |
| 4,747,395 A | 5/1988 | Brief | |
| 4,765,311 A | 8/1988 | Kulik et al. | |
| 4,817,587 A | 4/1989 | Janese | |
| 4,852,552 A | 8/1989 | Chaux | |
| 4,862,891 A | 9/1989 | Smith | |
| 4,899,729 A | 2/1990 | Gill et al. | |
| 5,027,793 A | 7/1991 | Engelhardt et al. | |
| 5,052,373 A | 10/1991 | Michelson | |
| 5,125,396 A | 6/1992 | Ray | |
| 5,139,511 A | 8/1992 | Gill et al. | |
| 5,158,545 A | 10/1992 | Trudell et al. | |
| 5,163,949 A | 11/1992 | Bonutti | |
| 5,197,971 A | 3/1993 | Bonutti | |
| 5,299,563 A | 4/1994 | Seton | |
| 5,312,417 A | 5/1994 | Wilk | |
| 5,339,803 A | 8/1994 | Mayzels et al. | |
| 5,353,784 A | 10/1994 | Nady-Mohamed | |
| 5,389,080 A | 2/1995 | Yoon | |
| 5,490,819 A | 2/1996 | Nicholas et al. | |
| 5,503,617 A | 4/1996 | Jako | |
| 5,509,893 A | 4/1996 | Pracas | |
| 5,512,038 A | 4/1996 | O'Neal et al. | |
| 5,549,595 A | 8/1996 | Freitas | |
| 5,573,517 A | 11/1996 | Bonutti et al. | |
| 5,618,260 A * | 4/1997 | Caspar et al. | 600/210 |
| 5,667,481 A | 9/1997 | Villalta et al. | |
| 5,674,240 A | 10/1997 | Bonutti et al. | |
| 5,681,265 A | 10/1997 | Maeda et al. | |
| 5,688,223 A | 11/1997 | Rosendahl | |
| 5,707,359 A | 1/1998 | Bufalini | |
| 5,728,046 A | 3/1998 | Mayer et al. | |
| 5,755,732 A | 5/1998 | Green et al. | |
| 5,776,054 A | 7/1998 | Bobra | |
| 5,779,629 A | 7/1998 | Hohlen | |
| 5,785,648 A | 7/1998 | Min | |
| 5,795,291 A | 8/1998 | Koros et al. | |
| 5,813,978 A | 9/1998 | Jako | |
| 5,823,947 A | 10/1998 | Yoon et al. | |
| 5,865,731 A | 2/1999 | Lenox et al. | |
| 5,888,196 A | 3/1999 | Bonutti | |
| 5,928,139 A | 7/1999 | Koros et al. | |
| 5,931,777 A | 8/1999 | Sava | |
| 5,944,658 A | 8/1999 | Koros et al. | |
| 5,951,466 A | 9/1999 | Segermark et al. | |
| 5,961,499 A | 10/1999 | Bonutti et al. | |
| 5,976,146 A | 11/1999 | Ogawa et al. | |
| 6,027,518 A | 2/2000 | Gaber | |
| 6,042,540 A | 3/2000 | Johnston et al. | |
| 6,074,343 A * | 6/2000 | Nathanson et al. | 600/214 |
| 6,074,380 A | 6/2000 | Byrne et al. | |
| 6,083,154 A | 7/2000 | Liu et al. | |
| 6,096,046 A | 8/2000 | Weiss | |
| 6,099,547 A | 8/2000 | Gellman et al. | |
| 6,139,493 A * | 10/2000 | Koros et al. | 600/215 |
| 6,149,583 A | 11/2000 | Vierra et al. | |
| 6,162,236 A | 12/2000 | Osada | |
| 6,171,299 B1 | 1/2001 | Bonutti | |
| 6,187,000 B1 | 2/2001 | Davison et al. | |
| 6,196,969 B1 * | 3/2001 | Bester et al. | 600/224 |
| 6,200,322 B1 | 3/2001 | Branch et al. | |
| 6,224,545 B1 * | 5/2001 | Cocchia et al. | 600/233 |
| 6,296,609 B1 | 10/2001 | Brau | |
| 6,312,443 B1 | 11/2001 | Stone | |
| 6,325,812 B1 | 12/2001 | Dubrul et al. | |
| 6,361,492 B1 | 3/2002 | Santilli | |
| 6,371,911 B1 | 4/2002 | Hossain et al. | |
| 6,394,950 B1 | 5/2002 | Weiss | |
| 6,431,025 B1 | 8/2002 | Koros et al. | |
| 6,450,952 B1 | 9/2002 | Rioux et al. | |
| 6,602,189 B1 | 8/2003 | Bennetti et al. | |
| 6,616,605 B2 | 9/2003 | Wright et al. | |
| 6,945,933 B2 | 9/2005 | Branch et al. | |
| 2003/0055319 A1 | 3/2003 | Chang | |
| 2004/0002629 A1 | 1/2004 | Smtih et al. | |
| 2004/0230191 A1 | 11/2004 | Frey et al. | |
| 2005/0113644 A1 | 5/2005 | Obenchain et al. | |
| 2005/0192485 A1 | 9/2005 | Branch et al. | |
| 2005/0234304 A1 | 10/2005 | Dewey et al. | |
| 2006/0069315 A1 | 3/2006 | Miles et al. | |

FOREIGN PATENT DOCUMENTS

| | | |
|---|---|---|
| EP | 9 856 286 A1 | 8/1998 |
| EP | 0 951 868 A1 | 10/1999 |
| EP | 1 192 905 | 9/2001 |
| FR | 1 019 217 A | 1/1952 |
| FR | 2 788 958 | 8/2000 |
| FR | 2 807 313 | 10/2001 |

* cited by examiner

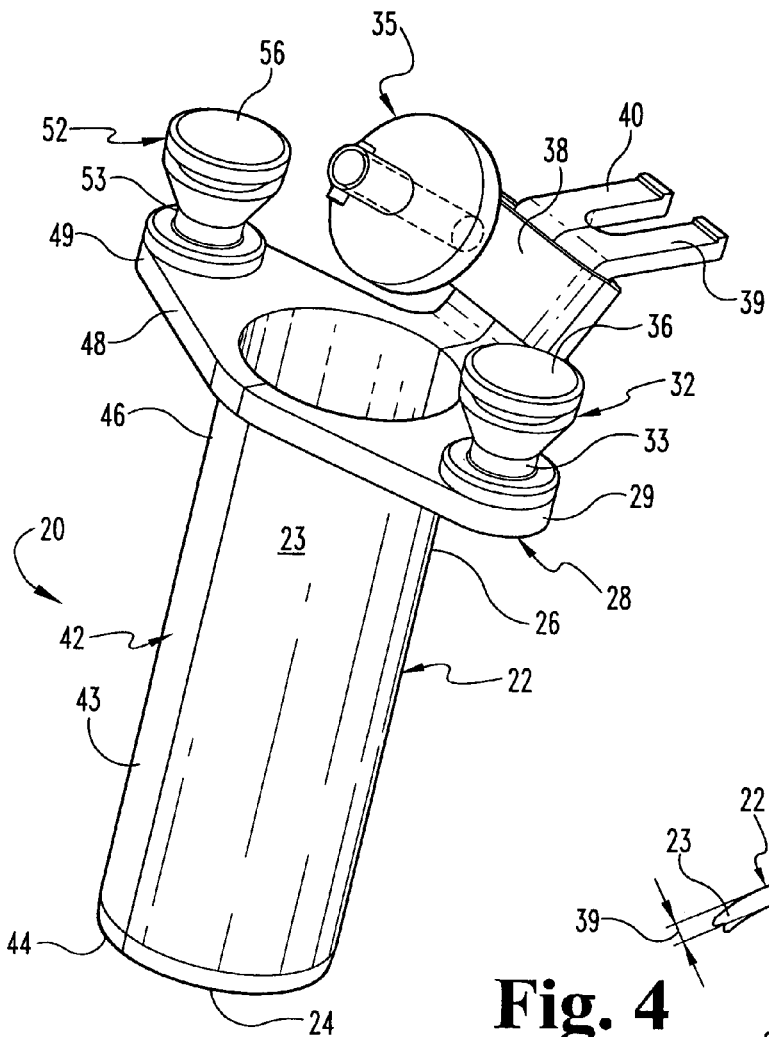
Fig. 3
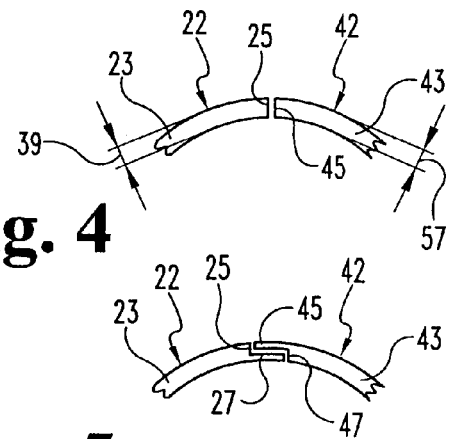
Fig. 4
Fig. 5
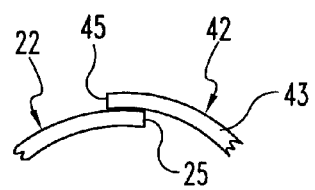
Fig. 6

INSTRUMENTS AND METHODS FOR MINIMALLY INVASIVE TISSUE RETRACTION AND SURGERY

CROSS-REFERENCE TO RELATED APPLICATION

This application is a continuation-in-part of U.S. patent application Ser. No. 10/180,658 filed on Jun. 26, 2002 and now issued as U.S. Pat. No. 6,945,933.

BACKGROUND

The present invention relates to instruments and methods for performing tissue retraction and surgeries through the retracted tissue in minimally invasive procedures.

Traditional surgical procedures for pathologies located within the body can cause significant trauma to the intervening tissues. These procedures often require a long incision, extensive muscle stripping, prolonged retraction of tissues, denervation and devascularization of tissue. These procedures can require operating room time of several hours and several weeks of post-operative recovery time due to the destruction of tissue during the surgical procedure. In some cases, these invasive procedures lead to permanent scarring and pain that can be more severe than the pain leading to the surgical intervention.

The development of percutaneous procedures has yielded a major improvement in reducing recovery time and post-operative pain because minimal dissection of tissue, such as muscle tissue, is required. For example, minimally invasive surgical techniques are desirable for spinal and neurosurgical applications because of the need for access to locations within the body and the danger of damage to vital intervening tissues. While developments in minimally invasive surgery are steps in the right direction, there remains a need for further development in minimally invasive surgical instruments and methods.

SUMMARY

The present invention is directed to methods and instruments for performing surgery in a patient. One specific application concerns instruments and methods for tissue retraction in minimally invasive spinal surgery. A further specific application includes instruments for percutaneous tissue retraction to provide access to a surgical location in the patient. Another specific application includes surgical methods performed through the percutaneously retracted tissue at any location in a patient's body. Other applications of the invention will also be apparent from the following description of the illustrated embodiments.

BRIEF DESCRIPTION OF THE FIGURES

FIG. 3 is a perspective of another embodiment retractor in an insertion configuration.

FIG. 4 is a detailed view of one configuration of adjacent retractor portions in an insertion configuration.

FIG. 5 is a detailed view of another configuration of adjacent retractor portions in an insertion configuration.

FIG. 6 is a detailed view of another configuration of adjacent retractor portions in an insertion configuration.

DESCRIPTION OF THE ILLUSTRATED EMBODIMENTS

Figures 1, 2:
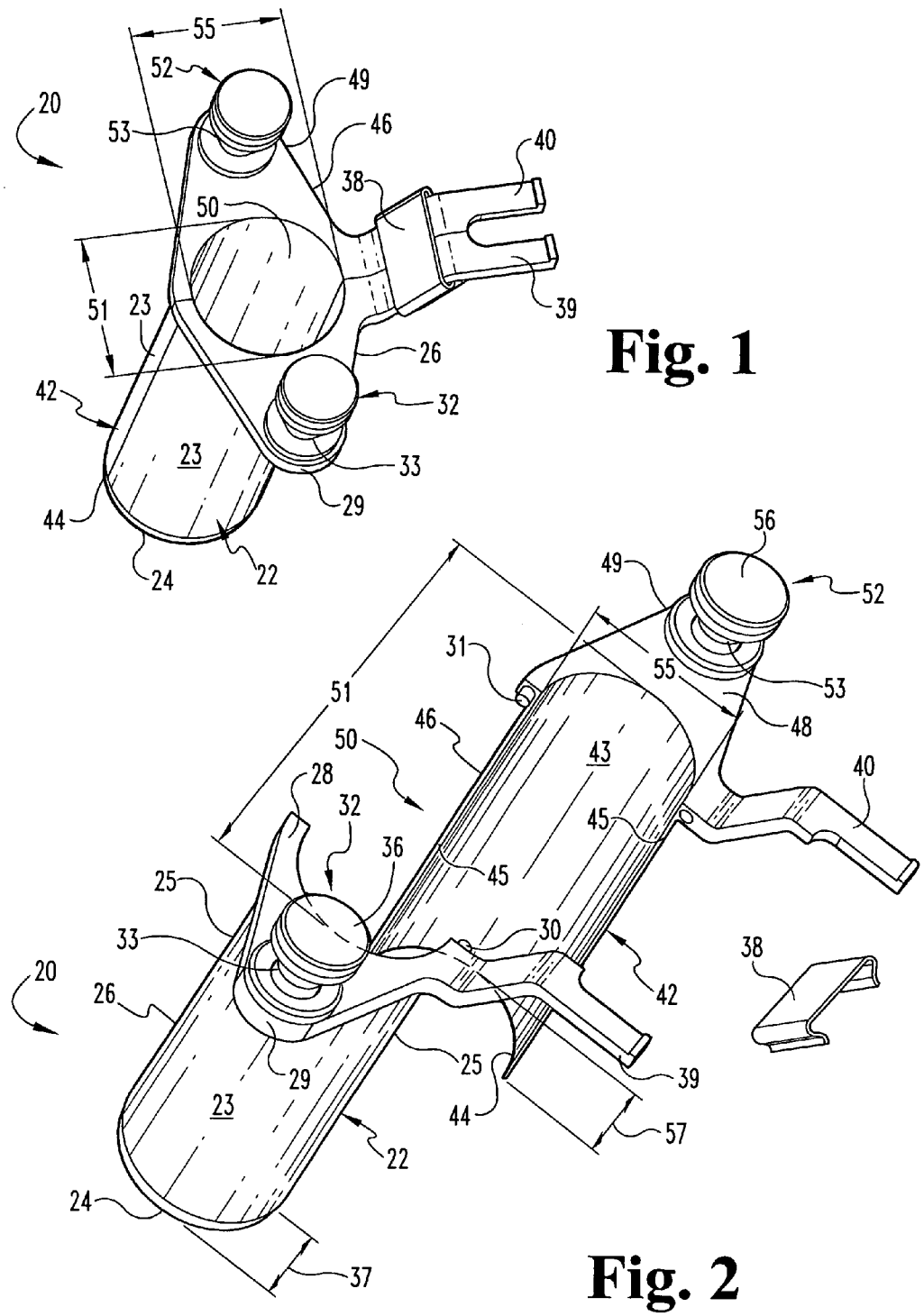
FIG. 1 is a perspective view of one embodiment retractor in an insertion configuration.
FIG. 2 is a perspective view of the retractor of FIG. 1 with first and second portions of the retractor separated from one another.

For the purposes of promoting an understanding of the principles of the invention, reference will now be made to the embodiments illustrated in the drawings and specific language will be used to describe the same. It will nevertheless be understood that no limitation of the scope of the invention is thereby intended. Any such alterations and further modifications in the illustrated devices and described methods, and any such further applications of the principles of the invention as illustrated herein are contemplated as would normally occur to one skilled in the art to which the invention relates.

The present invention provides instruments and methods for performing percutaneous surgery, including spinal surgeries that include one or more techniques such as laminotomy, laminectomy, foramenotomy, facetectomy, discectomy, interbody fusion, spinal nucleus or disc replacement, and implant insertion, for example. The surgery is performed through a working channel or passageway through skin and tissue of the patient provided by a retractor. Viewing of the surgical site at the working end of the retractor can be accomplished with viewing instruments mounted on the retractor, positioned over the retractor, and/or through a viewing system such as lateral fluoroscopy. The retractor is movable in situ to increase the size of the working channel to facilitate access to the working space at the distal end of the retractor while minimizing trauma to tissue surrounding the retractor. The retractor can be used with any surgical approach to the spine, including anterior, posterior, posterior mid-line, lateral, postero-lateral, and/or antero-lateral approaches, and in other regions besides the spine.

In FIG. 1 there is illustrated a retractor 20 that includes a first portion 22 and a second portion 42. First portion 22 has a distal end 24 and an opposite proximal end 26. Second portion 42 has a distal end 44 and an opposite proximal end 46. Distal ends 24, 44 can be beveled to facilitate insertion, although non-beveled ends are also contemplated. First portion 22 can be positioned adjacent to or mated with second portion 42 along adjacent ones of the longitudinal edges 25 of first portion 22 and longitudinal edges 45 of second portion 42. A working channel 50 is formed between first portion 22 and second portion 42. Working channel 50 extends between and opens at distal ends 24, 44 and proximal ends 26, 46.

Retractor 20 is insertable through skin and tissue of a patient to provide working channel 50 to the surgical site. It is contemplated that retractor 20 is inserted through the skin and tissue in an insertion configuration for working channel 50, such as shown in FIG. 1. In the insertion configuration, working channel 50 is substantially enclosed or circumscribed by first portion 22 and second portion 42. After insertion into the patient, working channel 50 can be enlarged by separating first portion 22 and second portion 42. Separation of first and second portions 22, 42 increases the size of working channel 50 from proximal ends 26, 46 to distal ends 24, 44.

In the insertion configuration of FIG. 1, working channel 50 is circumscribed or substantially enclosed by first portion 22 and second portion 42. Working channel 50 can have a size in the insertion configuration that allows passage of one or more surgical instruments and/or implants to the surgical location in the patient's body. It may be desirable during surgery to provide greater access to the location in the patient's body beyond the locations provided through working channel 50 in its insertion configuration. First portion 22 and second portion 42 are movable away from one another to enlarge working channel 50. In the enlarged configuration of working channel 50, a space is formed between at least of the adjacent longitudinal edges 25, 45 of first and second portions 22, 42. The space between the adjacent longitudinal edges 25, 45 exposes enlarged working channel 50 to skin and tissue of the patient between the separated first portion 22 and second portion 42. This exposed tissue can also be accessed by the surgeon through the enlarged working channel 50 with one or more instruments and/or implants. It is further contemplated that a shield, guard or tissue retractor could be placed in enlarged working channel 50 to maintain the exposed tissue away from the enlarged working channel 50.

First portion 22 includes a semi-cylindrical body 23 extending between distal end 24 and proximal end 26. A collar 28 extends about proximal end 26, and forms a lip extending about the outer surface of body 23. First portion 22 includes a first bracket member 39 extending from proximal end 26. Second portion 42 includes a semi-cylindrical body 43 extending between distal end 44 and proximal end 46. A collar 48 extends about proximal end 46 of second portion 42, and defines a lip extending about the outer surface of body 43. Second portion 42 includes a second bracket member 40 extending from proximal end 46.

A first alignment member 30 can be provided to couple a first side of first portion 22 to second portion 42 adjacent proximal ends 26, 46. A second alignment member 31 opposite first alignment member 30 can be provided to couple the other side of first portion 22 to second portion 42 adjacent proximal ends 26, 46 along another side of retractor 20. Holding member 38 can be positioned about bracket members 39, 40 to hold first portion 22 and second portion 42 adjacent one another. In one embodiment, alignment members 30, 31 are pins slidably received in holes 43 (only one shown in FIG. 2) formed in the other retractor portion when retractor 20 is in its insertion configuration. Alignment members 30, 31 maintain first portion 22 and second portion 42 in longitudinal alignment with one another during and after insertion. Holding member 38 can be resiliently biased to engage bracket members 39, 40 and maintain first portion 22 and second portion 42 adjacent one another during and after insertion. Holding member 38 can be removed from bracket members 39, 40 when it is desired to separate first and second portions 22, 42.

Other arrangements are also contemplated for aligning and releasably coupling first portion 22 and second portion 42 to one another. Examples of such arrangements include dovetail connections, fasteners, threaded coupling members, clamping members, snap rings, compression bands, straps, ball-detent mechanisms, and releasably interlocking cams or tabs, for example. Examples of suitable holding members include clamps, clips, bands, straps, hooks, ties, sleeves, coupling members and/or fasteners. As shown in FIG. 3, holding member 38 can be provided with a clamping mechanism 35 to bias holding member 38 into engagement with bracket members 39, 40. Clamping mechanism 35 can include a thumb wheel and threaded shaft that bears against one or both of the bracket members 39, 40 to solidly attach holding member 38 thereto and provide a quick disconnect of holding member 38 from bracket members 39, 40.

Figure 7:
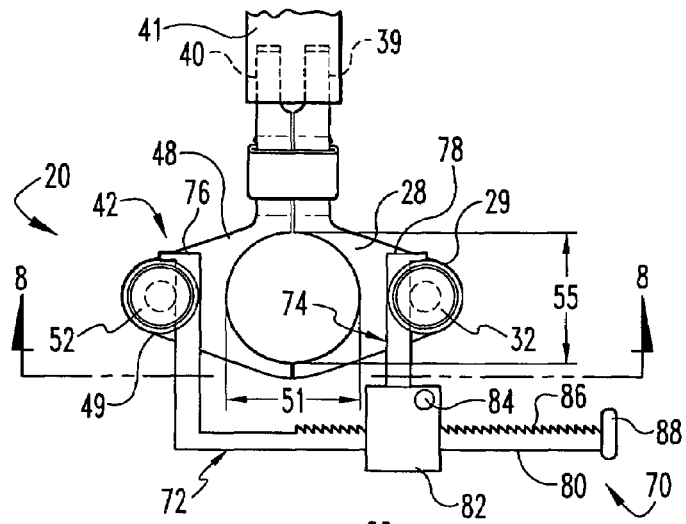
FIG. 7 is a plan view of the retractor of FIG. 1 in an insertion configuration with an instrument for separating first and second portions of the retractor coupled thereto.

Bracket member 39 and 40 can extend from and be integrally formed with or attached to respective ones of the collars 28, 48 of first and second portions 22, 42. Bracket members 39, 40 can also be provided as a single bracket on one of the collars 28, 48 in lieu of or in addition to bracket members 39, 40. Bracket members 39, 40 extend away from working channel 50 and are connectable to one end of a flexible or articulatable arm 41 (FIG. 7.) The opposite end of arm 41 (not shown) can be mounted on the surgical table or other support device. Arm 41 supports retractor 20 in the patient yet allows percutaneous manipulation and re-positioning of retractor 20 during surgery. It is further contemplated that more than one flexible arm 41 can be provided to engage respective ones of the retractor portions 22, 42 after enlargement of working channel 50.

With working channel 50 of retractor 20 in its insertion configuration, the opposite edges 25 of first portion 22 are adjacent respective ones of the opposite edges 45 of second portion 42. Various interfaces between the edges 25, 45 are contemplated. For example, in FIG. 4 there is shown a configuration in which edges 25 (only one shown) of first portion 22 abut along all or a portion of the adjacent edge 45 of second portion 42 in the insertion configuration for working channel 50. In FIG. 5 there is another embodiment first portion 22 having an outer recess 27 along each of the edges 25 (only one shown.) Each of the edges 45 can include an inner recess 47. Edges 25, 45 can thus interdigitate and abut one another in recesses 27, 47 in the insertion configuration for working channel 50. In FIG. 6 there is shown an overlapping arrangement in which edges 25 (only one shown) of first portion 22 can be located inside, relative to working channel 50, the adjacent edge 45 of second portion 42. It is also contemplated that edge 45 could be located inside edge 25. It is further contemplated that on one side of retractor 20 edge 25 can be inside edge 45, and on the other side of retractor 20 the other edge 45 can be inside the other edge 25. Other arrangements contemplate a gap between adjacent ones of the edges 25, 45.

Body 23 has a perimeter length along distal end 24 which can be about the same as the perimeter length of body 23 at proximal end 26. Body 43 of second portion 42 includes a perimeter length along distal end 44 which can be about the same as the perimeter length of body 43 adjacent proximal end 46. Bodies 23, 43 can have a semi-circular cross-section, and form a generally circular cross-section for the working channel when placed adjacent one another, as shown in FIG. 1. Other cross-sectional shapes are also contemplated for first and second portions 22, 42, such as, for example, any open sided polygonal shape, curved shape, or combined curved/polygonal shape.

Extending proximally from collar 28 of first portion 22 is a first engagement member 32 having a head portion 36 forming a recess 33 therebelow. Extending proximally from collar 48 of second portion 42 is a second engagement member 52 having a head portion 56 forming a recess 53 therebelow. Head portions 36, 56 can be threadingly engaged, reciprocally engaged and spring biased toward collars 28, 48, or otherwise engaged to the respective collar 28, 48 and adjustable to increase and decrease the height of the respective recess 33, 53 to receive and couple a separation instrument therein. It is also contemplated that engagement members 32, 52 can be non-adjustable, and the separation instrument configured to engage the adjacent engagement member 32, 52.

As discussed further below, an instrument for separating first portion 22 and second portion 42 can be non-releasably or releasably engaged to engagement members 32, 52 for application of a separation force to enlarge working channel 50 by separating first portion 22 and second portion 42. Such an instrument could also be releasable or non-releasably engaged to first portion 22 and second portion 42. Such an instrument could also maintain first portion 22 and second portion 42 in the initial insertion configuration and/or in the enlarged configuration for working channel 50. Other means besides the separation instrument could also be employed for maintaining first portion 22 and second portion 42 in one or both of the initial insertion configuration and the enlarged configuration for working channel 50. For example, when the separation instrument is not attached, a member could extend between and be coupled to each of the engagement members 32, 52 and/or retractor portions 22, 42.

Engagement members 32, 52 are positioned on lateral extensions 29, 49 of collars 28, 48, respectively. Lateral extensions 29, 49 extend far enough laterally to allow engagement of a separation instrument to engagement members 32, 52 without obstructing working channel 50 with the separation instrument.

It is contemplated that body 23 can be provided with a thickness 39 (FIG. 4.) Body 43 of second portion 42 can be provided with a thickness 59 (FIG. 4) that can be the same, greater than, or less than thickness 39 of first portion 22. Bodies 23, 43 can be provided with sufficient rigidity between their distal and proximal ends to separate and maintain separation of body tissue when retractor is initially inserted and also when tissue is retracted by moving first portion 22 and second portion 42 away from one another. First thickness 39 and second thickness 59 can provide first portion 22 and second portion 42, respectively, with sufficient rigidity to resist bending or bowing under the forces exerted on it by the retracted tissue. Also, body 23 has a depth 37 from edges 25 to the midpoint of wall of body 23 extending between edges 25. Depth 37 can provide a sufficient section modulus or moment of inertia in the direction of movement of first portion 22 to resist bending, bowing and/or deflection forces applied during such movement. Similarly, body 43 can have a depth 57 from edges 45 to the midpoint of wall of body 43 extending between edges 45 to provide a sufficient section modulus or moment of inertia in the direction of movement of second portion 42 to resist bending, bowing, and/or deflection forces applied during such movement.

In one specific embodiment, first portion 22 and second portion 42 are each made from surgical grade stainless steel. Other materials are also contemplated for first and second portions 22, 42, including, for example, plastics and metals and metal alloys, such as, for example, spring steel, shape memory metals and alloys, and aluminum.

Figure 8:
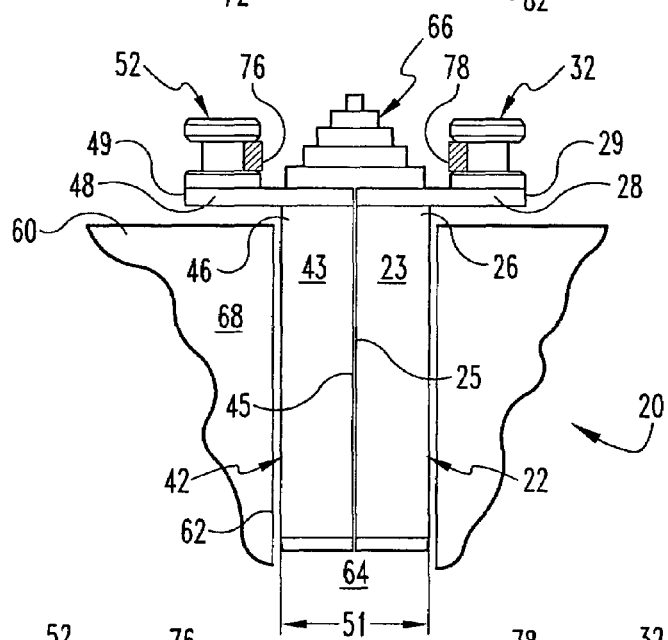
FIG. 8 is a section view through line 8-8 of FIG. 7 in which the retractor has been inserted over sequential tissue dilators.

In the initial insertion configuration, working channel 50 has a generally circular cross-section along retractor 20, as shown in FIGS. 1, 7 and 8. Working channel 50 has a first width 51 in the direction of movement of first portion 22 relative to second portion 42, and a second width 55 extending from one of the pair of adjacent edges 25, 45 to the other of the pair of adjacent edges 25, 45. In the illustrated embodiment, first and second widths 51 and 55 can be substantially the same since working channel 50 has a generally circular cross-section in its initial insertion configuration. In the enlarged configuration, as shown in FIGS. 2 and 9, second width 55 remains generally the same as in the initial insertion configuration for retractor 20, while first width 51 is increased by separating first portion 22 and second portion 42.

Various configurations for working channel 50 are contemplated. In the initial insertion configuration, working channel 50 can have a cylindrical shape with, for example, a circular, oval, elliptical, polygonal, or combined polygonal/curved cross-sectional shape. In the enlarged configuration, working channel 50 can have a cylindrical or frusto-conical shape with, for example a cross-section that is oval, elliptical, circular, curved, polygonal, or combined polygonal/curved in shape.

One specific application for retractor 20 is in spinal surgery. It is contemplated that, after insertion of retractor 20, first portion 22 and second portion 42 are separated predominantly in one direction to retract muscle and tissue along pathway 62 (FIG. 7.) For example, first and second portions 22, 42 of retractor 20 can be primarily or predominantly separable in the direction of the spinal column axis. The muscle tissue adjacent the spine has a fiber orientation that extends generally in the direction of the spinal column axis. The separation of body portions 23, 43 of retractor 20 can also separate the muscle tissue along the fibers, thus the amount of separation and the resultant tearing and trauma to the muscle tissue can be minimized. It is also contemplated in other techniques employing retractor 20 that working channel 50 can be enlarged primarily in a direction other than along the spinal column axis or in areas other than spine. Embodiments of retractor 20 are also contemplated in which working channel 50 is enlarged substantially in one direction or in all directions.

Figure 9:
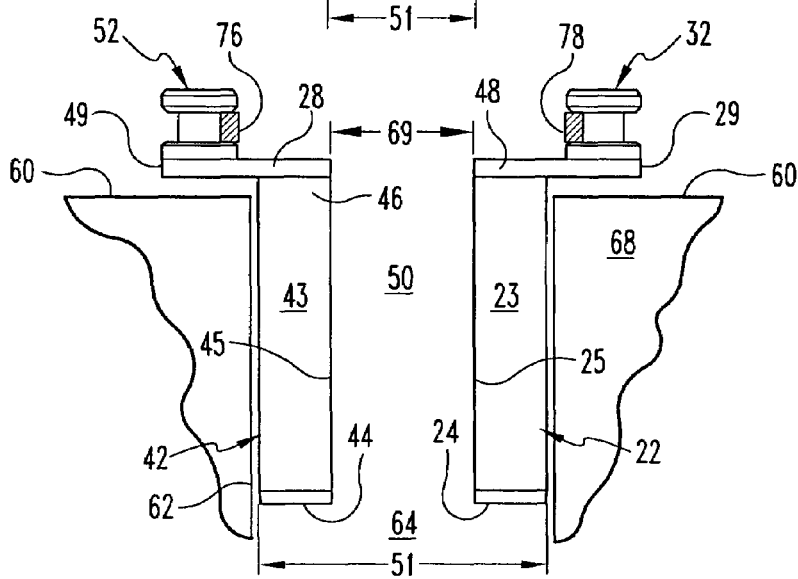
FIG. 9 is the retractor of FIG. 8 with the working channel of the retractor enlarged.

Referring now to FIGS. 7-9, one example of a method for positioning of retractor 20 through the skin 60 and tissue 68 of the patient will be described. An incision is made in skin 60 adjacent the location of a patient's anatomy to be accessed. For example, in spinal surgery, the incision can be made at a vertebral level at a location that provides access to the disc space between adjacent vertebrae or to one or more vertebra through a desired approach. Prior to insertion of retractor 20, skin 60 and tissue 68 can be sequentially dilated via dilation instrument set 66 which can include guidewires and/or one or more tissue dilators of increasing size. The tissue dilators are inserted one over another to form a pathway 62 through skin 60 and tissue 68 to the surgical site in the patient. In such procedures, retractor 20 is positioned over the last inserted dilator to form pathway 62 in the skin and tissue. Working channel 50 through retractor 20 provides access to a working space 64 at the distal end of retractor 20 when the guidewires and dilators, if used, are removed therefrom.

For the entire surgery or for certain procedures during the surgery, it may be desired by the surgeon to increase the size of working channel 50 to facilitate access working space 64 below the distal end of retractor 20, or to increase the size of working space 64. First and second portions 22, 42 of retractor 20 can be separated from their insertion configuration to a separated configuration in which working channel 50 is enlarged, as shown in FIG. 9. In the enlarged configuration, first portion 22 and second portion 42 can be moved laterally and/or pivoted away from one another by a separation instrument. One example of a separation instrument is separation instrument 70 extending between and coupled to engagement members 32, 52. Adjacent ones of the edges 25, 45 are separated by a space 69, exposing working channel 50 to the skin and tissue along pathway 62 while first and second portions 22, 42 hold tissue out of the operative field. In the enlarged configuration, working channel 50 and thus pathway 62 are enlarged through the through skin 60 and tissue 68 formed by first portion 22 and second portion 42. The size of working space 64 can be increased while minimizing trauma to the tissue and skin along pathway 62.

First and second portions 22, 42 can be pivoted or rotated away from one another about their proximal ends to provide working channel 50 with a tapered configuration that reduces in size from the distal end of retractor 20 adjacent working space 64 through skin 60 to the proximal end of retractor 20. A tapered working channel provides the surgeon greater access and increased visualization of working space 64 while minimizing tissue retraction. The tapered working channel 50 also allows greater angulation of instruments and implants placed through working channel 50, more selection in positioning of instruments and implants within working channel 50, and the ability to position instruments and implants adjacent the inner wall surfaces of the separated first and second portions 22, 42, increasing the room available at working space 64 for multiple instruments and for orienting implants.

Viewing instruments can be positioned in or adjacent to working channel 50 to facilitate surgeon viewing of working space 64 and the operative site. For example, an endoscopic viewing element can be mounted on the proximal end of retractor 20 with a scope portion extending along working channel 50. A microscopic viewing element can be positioned over the proximal end of retractor 20 for viewing working space 64 and the surgical site. Other imaging techniques, such as lateral fluoroscopy, can be used alone or in combination with the endoscopic and microscopic viewing elements. It is further contemplated that other instruments can be mounted on the proximal end of retractor 20, such as nerve root retractors, tissue retractors, forceps, cutter, drills, scrapers, reamers, separators, rongeurs, taps, cauterization instruments, irrigation and/or aspiration instruments, illumination instruments, inserter instruments, and the like for use in surgical procedures through retractor 20 in the working space. Such viewing instruments and other instruments can be employed with working channel 50 in its initial insertion configuration and/or its enlarged configuration.

Referring now to FIG. 7, further details regarding one embodiment instrument 70 for separating first and second portions 22, 42 will be provided. Instrument 70 includes a rack portion 72 and a body portion 74. Rack portion 72 includes a foot portion 76 releasably engageable to engagement member 52, and body portion 74 includes a foot portion 78 releasably engageable to engagement member 32. Rack portion 72 includes an extension 80 received through a housing 82 of body portion 74. Housing 82 includes a pinion 84 rotatably mounted therein and engaged with teeth 86 of extension 80. Pinion 84 can be engaged by a tool or manually by the surgeon and rotated to move rack portion 72 relative to body portion 74, thereby moving feet portion 76, 78 away from one another to separate first portion 22 and second portion 42 to enlarge working channel 50. A stop member 88 can be provided at the end of or at any position along extension 80 to prevent over-separation of first portion 22 and second portion 42.

Figure 10:
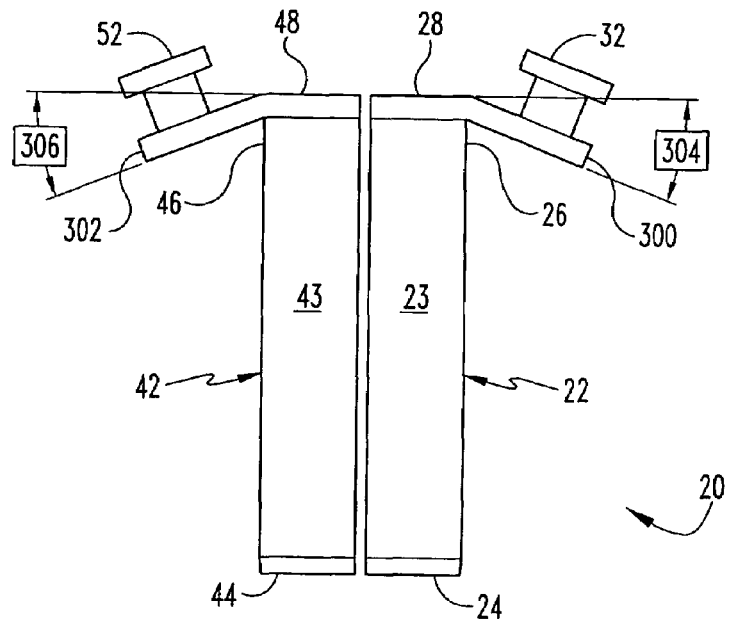
FIG. 10 is a side view of another embodiment retractor in an insertion configuration.
Figure 11:
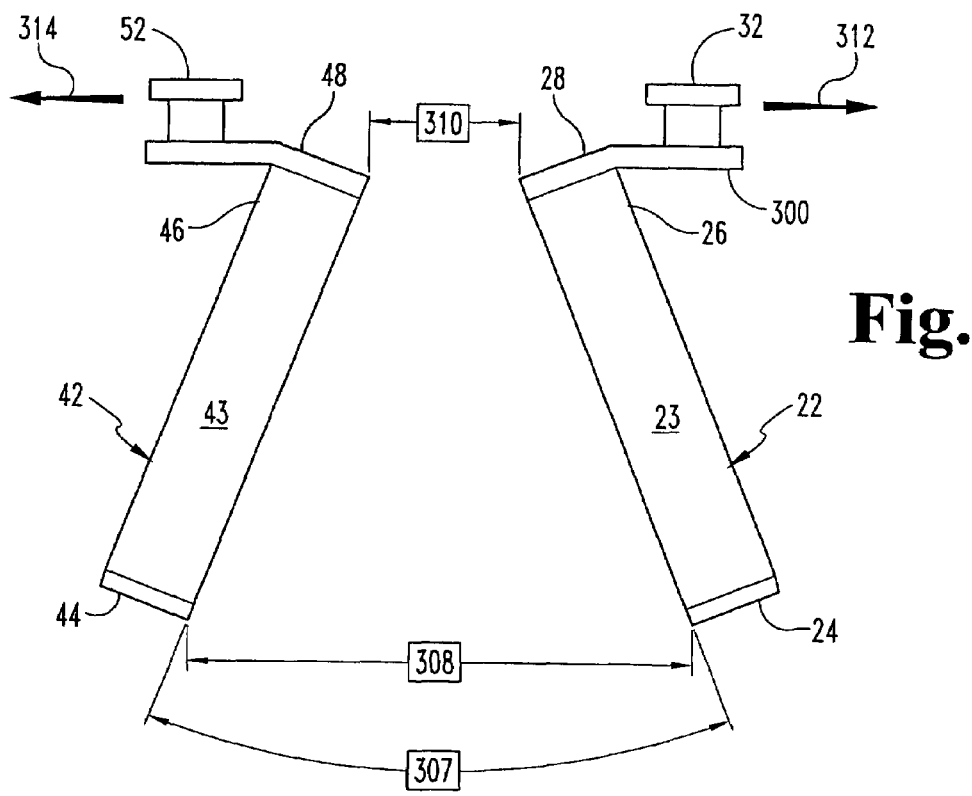
FIG. 11 is the retractor of FIG. 10 with the working channel enlarged.

Referring now to FIGS. 10 and 11, another embodiment retractor 20 is shown in which retractor portions 22, 42 are simultaneously separable from one another and pivotal relative to one another to enlarge working channel 50. Collar 28 includes an extension 300 extending from body 23 of first portion 22 generally in the direction of separation of first portion 22 from second portion 42. Collar 48 includes an extension 302 extending from body 43 of second portion 42 generally in the direction of separation of second portion 42 from first portion 22. In the insertion configuration of FIG. 10, extension 300 extends distally from collar 28 at an angle 304, and extension 302 extends distally from collar 48 at an angle 306. Engagement members 32, 52 extend proximally from respective ones of the extensions 300, 302.

In FIG. 11, working channel 50 has been enlarged by application of a lateral separation force with, for example, separation instrument 70 discussed above or instrument 220 discussed below, as indicated by arrows 312, 314. The lateral separation forces move first portion 22 away from second portion 42. The lateral separation forces are applied to the engagement members 32, 52 on the angled extensions 300, 302. Angled extensions 300, 302 tend to cause distal ends 24, 44 to pivot or rotate away from one another as angled extensions 300, 302 are rotated or pivoted in the direction in which lateral forces 314, 316 are applied. As a result, edges 25, 45 form angle 307 therebetween and provide working channel 50 with an enlarged, frusto-elliptical shape between the distal ends 24, 44 and proximal ends 26, 46. Distal ends 24, 44 are separated at edges 25, 45 by a distance 308, which is greater than the distance 310 separating edges 25, 45 adjacent proximal ends 26, 46.

Figure 12:
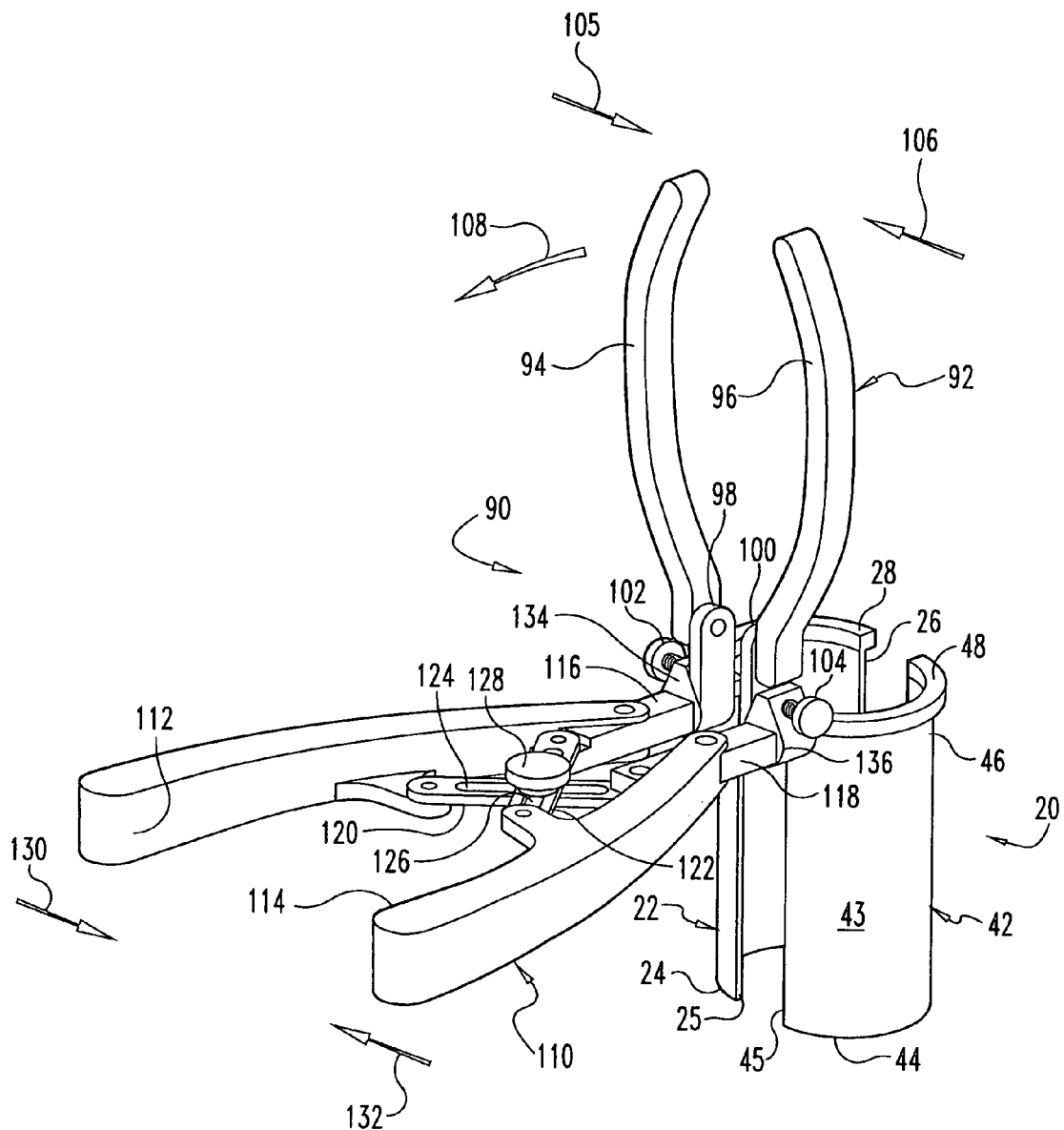
FIG. 12 is a perspective view of another embodiment retractor and instrument for separating first and second portions of the retractor.

Referring now to FIG. 12, there is shown retractor 20 with another embodiment instrument 90 for separating first portion 22 and second portion 42. Instrument 90 includes a rotational separator 92 and a lateral separator 110. Rotational separator 92 is operable to rotate or pivot first portion 22 and second portion 42 relative to one another about their proximal ends 26, 46 to move distal ends 24, 44 away from one another. Lateral separator 110 is operable to move first portion 22 and second portion 24 away from one another by separating proximal ends 26, 46 and distal ends 24, 44 laterally. As discussed further below, instrument 90 can be coupled to engagement members (not shown) of the first and second portions 22, 42 located adjacent one of the edges 25, 45 and extending laterally from the respective first and second portions 22, 42. Rotational separator 92 and lateral separator 110 can be operated sequentially to pivot then laterally separate, or laterally separate and then pivot first and second portions 22, 42. Rotational separator 92 and lateral separator 110 can also be operated simultaneously to pivot/rotate and laterally separate first and second portions 22, 42.

Rotational separator 92 includes a first handle 94 and a second handle 96. First handle 94 is mounted to a first coupling member 98, and second handle 96 is mounted to a second coupling member 100. First coupling member 98 of rotational separator 92 is non-rotatably coupled to the lateral engagement member of first portion 22, and second coupling member 100 of rotational separator 92 is non-rotatably coupled to the lateral engagement member of second portion 42. First and second portions 22, 42 are pivotal or rotatable away from one another by moving first handle 94 in the direction of arrow 105 toward second handle 96, and by moving second handle 96 in the direction of arrow 106 toward first handle 94. Movement of handles 94, 96 in the direction of arrows 105, 106 rotates the proximal ends of coupling members 98, 100 toward one another to effect the pivotal or rotational movement of first and second portions 22, 42. Handles 94, 96 can be pivotally coupled to connectors 98, 100 for rotation in the direction of arrow 108 to move handles 94, 96 away from the proximal end opening of working channel 50 and provide the surgeon clear access thereto.

Lateral separator 110 extends laterally from retractor 20 transversely to the direction of separation of first portion 22 and second portion 42. Lateral separator 110 includes a first handle 112 and a second handle 114. A first coupling member 116 is pivotally coupled at a mid-portion thereof to first handle 112, and a second coupling member 118 is pivotally coupled at a mid-portion thereof to second handle 114. Coupling members 116, 118 are rotationally coupled at their distal ends to respective ones of the lateral engagement members extending from first portion 22 and second portion 42. A first link 120 extends between and is pivotally coupled at one end to first handle 112 and at its opposite end to second coupling member 118. A second link 122 extends between and is pivotally coupled at one end to second handle 114 and at its opposite end to first coupling member 116. First coupling member 116 includes a first tab 134 that rotatably receives the lateral engagement member extending from first portion 22. Second coupling member 118 includes a second tab 136 that rotatably receives the lateral engagement member extending from second portion 42.

First link 120 includes a first slot 124, and second link 122 includes a second slot 126. A locking pin 128 extends through slots 124, 126 and couples links 120, 122 to one another. To laterally separate first portion 22 from second portion 42, locking pin 128 is loosened so the links 120, 122 are movable relative to one another. First handle 112 is moved in the direction of arrow 130 toward second handle 114, and second handle 114 is moved in the direction of arrow 132 toward first handle 112. First link 120 pushes outwardly on second coupling member 118 while second handle 114 pulls outwardly on second coupling member 118. Similarly, second link 122 pushes outwardly on first coupling member 116 while first handle 112 pulls outwardly on first coupling member 116. Coupling members 116, 118 thus laterally move away from one another. This separates first and second portions 22, 42 such that edges 25, 45 are displaced laterally the same relative distance from one another between proximal ends 26, 46 and distal ends 24, 44. Locking pin 128 can then be threaded to clamp link members 120, 122 together and prevent further movement of lateral separator 110. Movement of handles 112, 114 in the direction opposite arrows 130, 132 moves first and second portion 22, 42 toward one another, and, if pivoted, movement of handles 94, 96 toward one another can pivot first and second portions 22, 42 toward one another to reduce working channel 50 for easier removal of retractor 20 from the incision.

First and second adjustment mechanisms 102, 104 are provided for small incremental adjustment in the rotational positioning of first portion 22 and second portion 42, respectively. First adjustment mechanism 102 extends through first tab 134 and engages first coupling member 98. As first adjustment mechanism 102 is threaded toward first tab 134, the end of first adjustment mechanism 102 pushes on first coupling member 98, causing first coupling member 98 and first handle 94 along with first portion 22 to pivot or rotate relative first tab 134. Adjustment mechanism 102 can also engage first coupling member 98 to maintain first portion 22 in a pivoted or rotated position provided through first handle 94. Similarly, second adjustment mechanism 104 extends through second tab 136 and engages second coupling member 100. As second adjustment mechanism 104 is threaded toward second tab 136, the end of second adjustment mechanism 104 pushes on second coupling member 100, causing second coupling member 100 and second handle 96 along with second portion 42 to pivot or rotate relative second tab 136. Second adjustment mechanism 104 can also engage second coupling member 100 and maintain second portion 42 in a pivoted or rotated position provided through second handle 96.

In use, the resistance to retraction provided by the tissue may prevent distal ends 24, 44 from separating as far as proximal ends 26, 46 when a separation force is applied with lateral separator 110. Rotational separator 92 can be used to move distal ends 24, 44 away from one another to provide the desired separation between edges 25, 45 along the length of first and second portions 22, 42.

Figure 13:
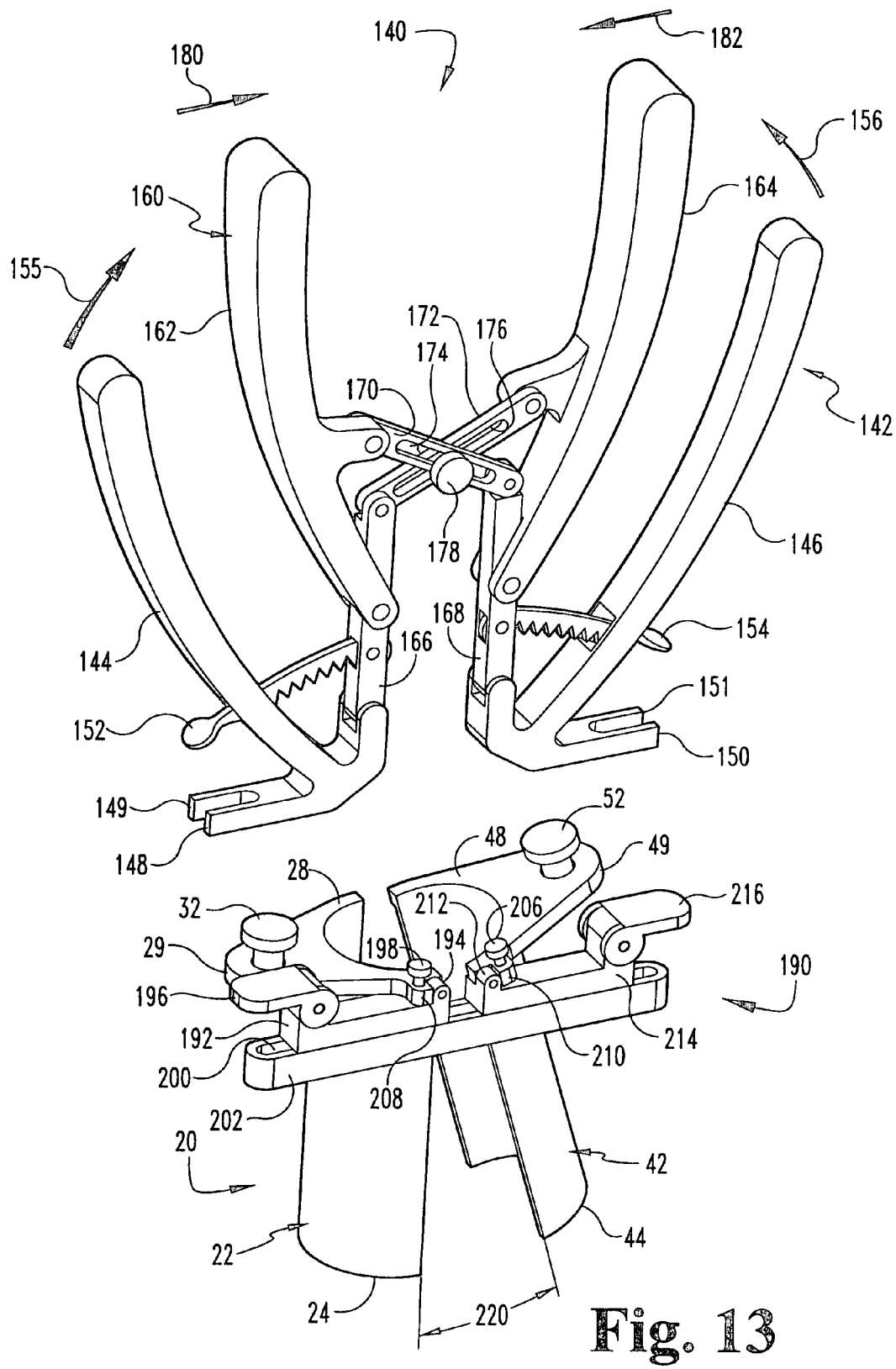
FIG. 13 is a perspective view of another embodiment retractor and instrument for separating first and second portions of the retractor.

Referring now to FIG. 13, there is shown retractor 20 with another embodiment instrument 140 for separating first portion 22 and second portion 42. Instrument 140 includes a rotational separator 142 and a lateral separator 160. Rotational separator 142 is operable to rotate or pivot first portion 22 and second portion 42 relative to one another about their proximal ends 26, 46 to move distal ends 24, 44 away from one another. Lateral separator 160 is operable to move first portion 22 and second portion 24 away from one another by separating proximal ends 26, 46 and distal ends 24, 44 laterally. Rotational separator 142 and lateral separator 160 can be operated sequentially to pivot then laterally separate, or laterally separate and then pivot first and second portions 22, 42. Rotational separator 142 and lateral separator 160 can also be operated simultaneously to pivot/rotate and laterally separate first and second portions 22, 42.

Rotational separator 142 includes a first handle 144 and a second handle 146. First handle 144 has a first coupling member 148, and second handle 146 has a second coupling member 150. First coupling member 148 includes a slot 149 to receive engagement member 32 of first portion 22, and second coupling member 150 includes a slot 151 to receive engagement member 52 of second portion 42. First and second portions 22, 42 are pivotal or rotatable away from one another by moving first handle 144 in the direction of arrow 155 toward second handle 146, and by moving second handle 146 in the direction of arrow 156 toward first handle 144.

Movement of handles 144, 146 in the direction of arrows 155, 156 moves coupling members 148, 150 away from one another to effect the pivotal or rotational movement of first and second portions 22, 42 relative to one another.

Lateral separator 160 includes a first handle 162 and a second handle 164. A first connector 166 is pivotally coupled at a mid-portion thereof to first handle 162, and a second connector 168 is pivotally coupled at a mid-portion thereof to second handle 164. Connectors 166, 168 are pivotally coupled at their distal ends to respective ones of first handle 144 and second handle 146 of rotational separator 142.

A first link 170 extends between and is pivotally coupled at one end to first handle 162 and at its opposite end to second connector 168. A second link 172 extends between and is pivotally coupled at one end to second handle 164 and at its opposite end to first connector 166. First connector 166 includes a first locking member 152 pivotally coupled thereto that can extend through and releasably engage first handle 144. Second connector 168 includes a second locking member 154 pivotally coupled thereto that can extend through and releasably engage second handle 146. Locking members 152, 154 can selectively engage and maintain the positioning of handles 142, 144 at any one of a number of positions to which first portion 22 and second portion 42 have been rotated or pivoted by rotational separator 142.

First link 170 includes a first slot 174, and second link 172 includes a second slot 176. A locking pin 178 extends through slots 174, 176 and couples links 170, 172 to one another. To laterally separate first portion 22 from second portion 42, locking pin 178 is loosened so links 170, 172 are movable relative to one another. First handle 162 is moved in the direction of arrow 180 toward second handle 164, and second handle 164 is moved in the direction of arrow 182 toward first handle 162. First link 170 pushes outwardly on second coupling member 168 while second handle 164 pulls outwardly on second coupling member 168. Similarly, second link 172 pushes outwardly on first coupling member 166 while first handle 162 pulls outwardly on first coupling member 166. Coupling members 166, 168 laterally move connecting portions 148 away from one another. Thus, actuation of handles 162, 164 laterally separates the connected first and second portions 22, 42 such that edges 25, 45 are laterally displaced relative to one another between proximal ends 26, 46 and distal ends 24, 44. Locking pin 178 can then be threaded to clamp link members 170, 172 together and prevent further movement of lateral separator 160. Movement of handles 162, 164 in the direction opposite arrows 180, 182 moves first and second portion 22, 42 toward one another to reduce the spacing therebetween for easier removal of retractor 20 from the incision.

In use, the resistance to retraction provided by the tissue may prevent distal ends 24, 44 from separating as far as proximal ends 26, 46 when a separation force is applied with lateral separator 160. Rotational separator 142 can be used to move distal ends 24, 44 away from one another to provide the desired separation between edges 25, 45 along the length of first and second portions 22, 42.

Instrument 140 is positioned over the proximal end opening of working channel 50. To provide clear access to working channel 50 for the surgeon, instrument 140 can be removed from retractor 20, and a guide mechanism 190 can maintain the lateral and rotational positioning of first portion 22 and second portion 42 obtained with instrument 140. Guide mechanism 190 includes a guide member 200 having a slot 202 formed therein. Guide member 200 extends between first portion 22 and second portion 42 along one side thereof, and first and second portions 22, 42 are coupled thereto. It is also contemplated that a second guide member could be provided on the other side of retractor 20.

A first coupling member 192 is movably mounted in slot 202 of guide member 200 adjacent first portion 22, and a second coupling member 214 is movably mounted in slot 202 of guide member 200 adjacent second portion 42. First portion 22 includes a first ear 208 extending from collar 28 pivotally coupled at one end 194 of first coupling member 192. At the other end of first coupling member 192 is a cam locking mechanism 196 that is releasably engageable to guide member 200 to maintain the positioning of first portion 22 along guide member 200. Second portion 42 includes a second ear 210 extending from collar 48 that is pivotally coupled at one end 212 of second coupling member 214. At the other end of second coupling member 214 is a cam locking mechanism 216 that is releasably engageable to guide member 200 to maintain the positioning of second portion 42 along guide member 200.

First and second adjustment mechanisms 198, 206 are provided for small incremental adjustment in the rotational positioning of first portion 22 and second portion 42, respectively. First adjustment mechanism 198 extends through first ear 208 and engages first coupling member 192. As first adjustment mechanism 198 is threaded toward first ear 208, the end of first adjustment mechanism 198 engages first coupling member 192, maintaining first portion 22 in its pivoted position relative to guide member 200. First adjustment mechanism 198 can also be manipulated by the surgeon for small adjustments in the pivotal position of first portion 22 relative to guide member 200 and second portion 42. Second adjustment mechanism 206 extends through second ear 210 and engages second coupling member 214. As second adjustment mechanism 206 is threaded toward second ear 210, the end of second adjustment mechanism 206 engages second coupling member 214 to maintain second portion 42 in its pivoted position relative to guide member 200. Second adjustment mechanism 206 can also be manipulated by the surgeon to make adjustments in the pivotal position of second portion 42 relative to guide member 200 and first portion 22.

Figure 14:
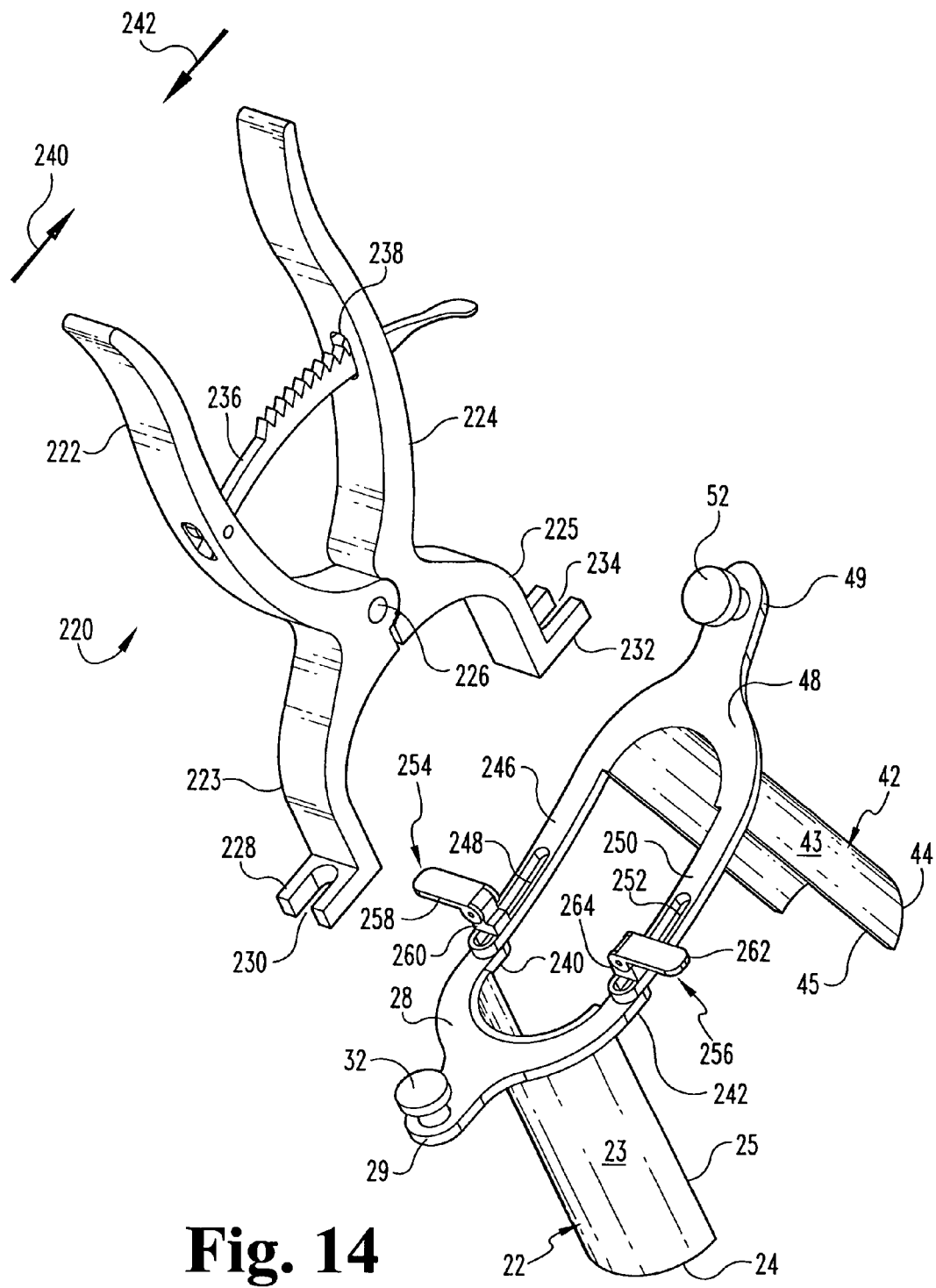
FIG. 14 is a perspective view of another embodiment retractor and instrument for separating first and second portions of the retractor.

Referring now to FIG. 14, there is shown another embodiment instrument 220 for separating first and second portions 22, 42 of retractor 20. Instrument 220 includes a first handle 222 pivotally coupled to a second handle 224 about pin 226. First handle 222 includes a distal portion 223 having a coupling member 228. Coupling member 228 includes a slot 230 for receiving engagement member 32 of first portion 22 therein. Second handle 224 includes a distal portion 225 having a coupling member 232. Coupling member 232 includes a slot 234 for receiving engagement member 52 of second portion 42 therein. A locking member 236 is pivotally coupled at one end to first handle 222, and extends through slot 238 of second handle 224 for releasable locking engagement therewith.

In use, instrument 220 is mounted on retractor 20 with coupling members 228, 232 in engagement with respective ones of engagement members 32, 52. Handles 222, 224 are moved toward one another in the direction indicated by arrows 240, 242 to move coupling members 228, 232 away from one another. In turn, first portion 22 and second portion 42 are separated from one another.

Retractor 20 can be adapted to guide first and second portions 22, 42 during separation and to maintain the separation provided with instrument 220. In the illustrated embodiment, collar 28 of first portion 22 includes opposite first and second ears 240, 242 extending beyond the adjacent edges 25 toward second portion 42. Second portion 42 includes first guide member 246 positionable over first ear 240, and second guide member 250 positionable over second ear 242. First guide member 246 includes a slot 248 and second guide member 250 includes a slot 252. A first cam locking mechanism 254 extends through slot 248 and couples first ear 240 to first guide member 248. A second cam locking mechanism 256 extends through slot 252 and couples second ear 242 to second guide member 250.

First cam locking mechanism 254 includes a lever 258 that clamps a locking body 260 against first ear 240 and first guide member 246, as shown in FIG. 14. Similarly, second cam locking mechanism 256 includes a lever 262 that clamps a locking body 264 against second ear 242 and second guide member 250, as shown in FIG. 14. When it is desired to move first portion 22 and/or second portion 42, levers 258 and 262 are rotated to release the respective clamped locking body 260, 264, respectively. Instrument 220 can then be used to apply a separation force, or first and second portions 22, 42 can be moved toward one another for easy removal from the incision.

It is contemplated that guide members 246, 250 can be curved or arcuate to follow the path of coupling members 228, 232 as coupling members 228, 232 are separated with handles 222, 224. In this manner, first portion 22 and second portion 42 are simultaneously pivoted/rotated and laterally separated with instrument 220. It is further contemplated that one or more guide members between first portion 22 and second portion 42 could be configured to provide only a lateral separation path or only a rotational separation path. Other embodiments contemplate guide members which provide a combined rotational and lateral separation path.

It is contemplated that for spinal surgery various retractors 20 can be provided in a kit with lengths ranging from 20 millimeters to 100 millimeters in increments of 10 or 20 millimeters. It is further contemplated that retractor 20 can be provided in a kit with various sized working insertion configurations, such as 14, 16, 18, 20, 21 or 25 millimeters for initial insertion width 55. It should be understood, however, that the present invention contemplates that retractor 20 can have other lengths and diameters and can be provided in a kit with different increments. The appropriate length for retractor 20 will depend on the depth of the desired surgical location below the skin of the patient, the anatomical location of the surgery, and the patient's anatomy. These factors in retractor selection can be evaluated through pre-operative planning prior to surgery by x-rays or other known imaging technique, and can be adjusted during the surgical procedure if necessary since retractors of differing lengths and working channel sizes can be made available.

Figure 16:
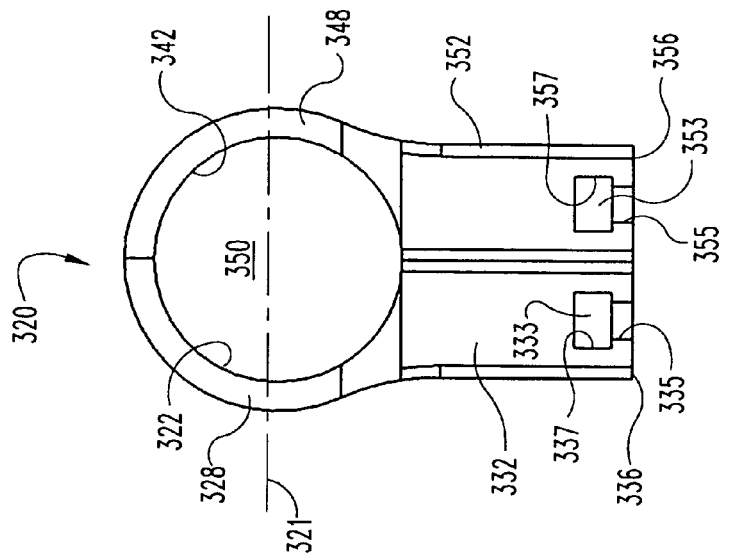
FIG. 16 is a plan view of the retractor of FIG. 15.
Figure 15:
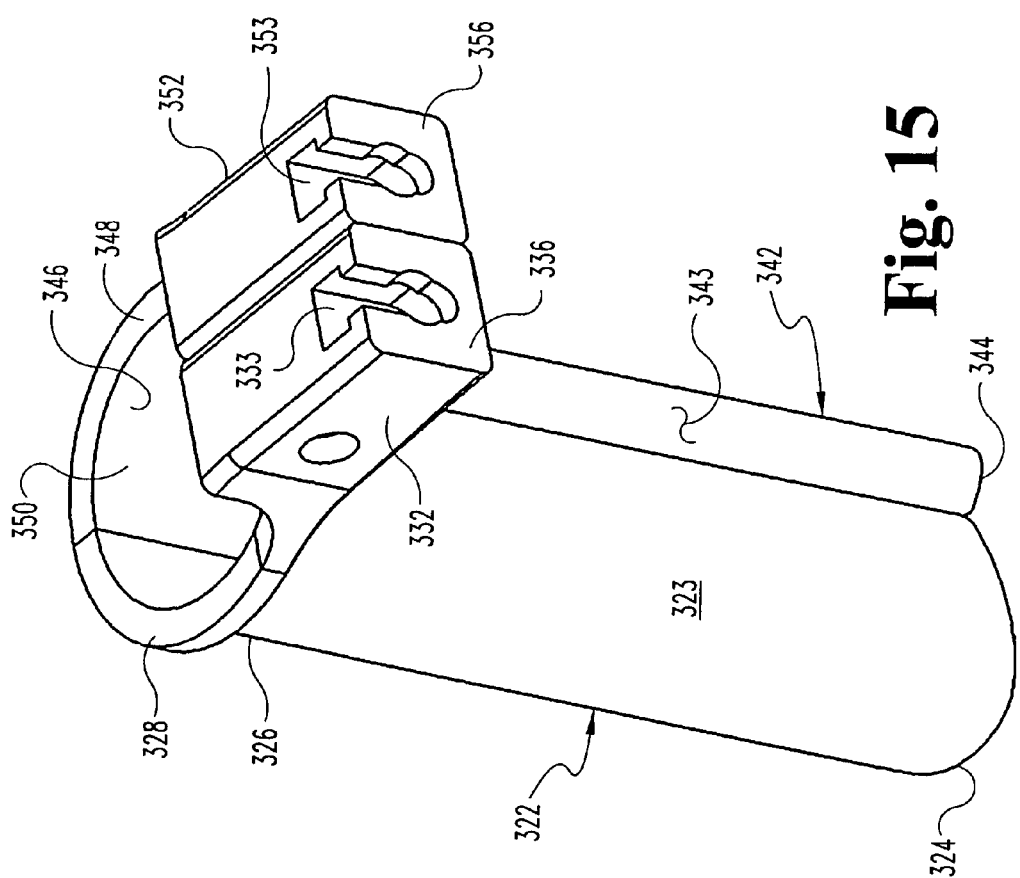
FIG. 15 is a perspective view of another embodiment retractor in an insertion configuration.

Referring to FIGS. 15 and 16, there is shown another embodiment retractor 320. Retractor 320 includes a first retractor portion 322 and a second retractor portion 342. First portion 322 includes a body 323 extending between a distal end 324 and an opposite proximal end 326. Second portion 342 includes a body 343 extending between a distal end 344 and an opposite proximal end 346. Distal ends 324, 344 can be beveled or distally tapered to facilitate insertion, although non-beveled ends are also contemplated. First portion 322 can be positioned adjacent to or mated with second portion 342 along adjacent ones of the longitudinal edges 325, 327 of first portion 322 and longitudinal edges 345, 347 of second portion 342. Other arrangements between the adjacent edges are also contemplated as discussed above. It is further contemplated that the longitudinal edges can be spaced from one another in the insertion configuration. A working channel 350 is formed between first portion 322 and second portion 342. Working channel 350 extends between and opens at distal ends 324, 344 and proximal ends 326, 346.

Retractor 320 is insertable through skin and tissue of a patient to provide working channel 350 to the surgical site. It is contemplated that retractor 320 is inserted through the skin and tissue in an insertion configuration for working channel 350, such as shown in FIGS. 15-18. In the insertion configuration, working channel 350 is substantially enclosed or circumscribed by first portion 322 and second portion 342. After insertion into the patient, working channel 350 can be enlarged by separating first portion 322 and second portion 342 away from one another along an axis 321 extending therebetween. Separation of first and second portions 322, 342 increases the size of working channel 350 from proximal ends 326, 346 to distal ends 324, 344.

In the insertion configuration of FIGS. 15-18, working channel 350 is circumscribed or substantially enclosed by first portion 322 and second portion 342. Bodies 323 and 343 can be configured as discussed above with respect to the bodies of the portions of retractor 20. Working channel 350 can have a size in the insertion configuration that allows passage of one or more surgical instruments and/or implants to the surgical location in the patient's body, although smaller sizes are also contemplated. It may be desirable during surgery to provide greater access to the location in the patient's body beyond the locations provided through working channel 350 in its insertion configuration. Accordingly, first portion 322 and second portion 342 are movable away from one another along axis 321 to enlarge working channel 350.

First portion 322 includes body 323 with a semi-cylindrical shape extending between distal end 324 and proximal end 326. A collar 328 extends about proximal end 326, and forms a lip extending about the outer surface of body 323. Second portion 342 includes body 343 having a semi-cylindrical shape extending between distal end 344 and proximal end 346. A collar 348 extends about proximal end 346 of second portion 342, and defines a lip extending about the outer surface of body 343. It is further contemplated that first and second portions 322, 342 can be provided with or without a collar and/or a lip. First and second portions 322, 342 can also be provided with bracket members for engagement with an external arm that supports retractor 320 while positioned in the patient.

Extending from collar 328 of first portion 322 is a first engagement member 332 having a head portion 336 forming a recess 333 therein. Extending from collar 348 of second portion 342 is a second engagement member 352 having a head portion 356 forming a recess 353 therein. Engagement members 332, 352 can be integrally formed with or removably engaged to the respective collars 328, 348. As discussed further below, an instrument for separating first portion 322 and second portion 342 can be non-releasably or releasably engaged to engagement members 332, 352 for application of a separation force to enlarge working channel 350 by separating first portion 322 and second portion 342. Such an instrument could also be releasably or non-releasably engaged to first portion 322 and second portion 342. Engagement members 332, 352 extend laterally from portions 322, 342 to facilitate allow engagement of a separation instrument to engagement members 332, 352 without obstructing working channel 350 with the separation instrument. Such an instrument could also maintain first portion 322 and second portion 342 in the initial insertion configuration during and after insertion. The separation instrument can also maintain the enlarged configuration for working channel 350 in situ.

Recesses 333, 353 are adapted to receive engagement arms of the separation instrument engageable to portions 322, 342. In the illustrated embodiments, engagement members 332, 352 extend laterally from and project proximally above the respective collar 328, 348. Engagement members 332, 352 extend alongside one another and abut one another when portions 322, 342 are in their insertion configuration. Other configurations for the engagement members are also contemplated, including engagement members that are non-linear, that extend in directions away from one another when portions 322, 324 are in their insertion configuration, and engagement members that do not abut one another in the insertion configuration.

Recesses 333, 353 open laterally to receive respective ones of the engagement arms of the separation instrument. Recess 333 includes a keyway opening 335 and a receptacle 337 in communication with opening 335. Receptacle 337 is enlarged relative to opening 335, and is shaped to receive a portion of the engagement arm of the separation instrument positioned therein. Similarly, recess 353 includes a keyway opening 355 and a receptacle 357 in communication with opening 355. Receptacle 357 is enlarged relative to opening 355, and is shaped to receive a portion of the engagement arm of the separation instrument positioned therein. Openings 335, 355 and receptacles 337, 357 are open along the proximal sides of the respective engagement members 332, 352 to facilitate placement of the separation instrument engagement arms therein. Other configurations for the recess 333, 353 are also contemplated, including recesses that are enclosed, uniform, or any other suitable configuration to receive a at least a portion of an engagement arm. Still other embodiments contemplate that engagement members 332, 352 do not include recesses, but rather are shaped for receipt in or otherwise engage the respective engagement arm of the separation instrument.

Figure 19:
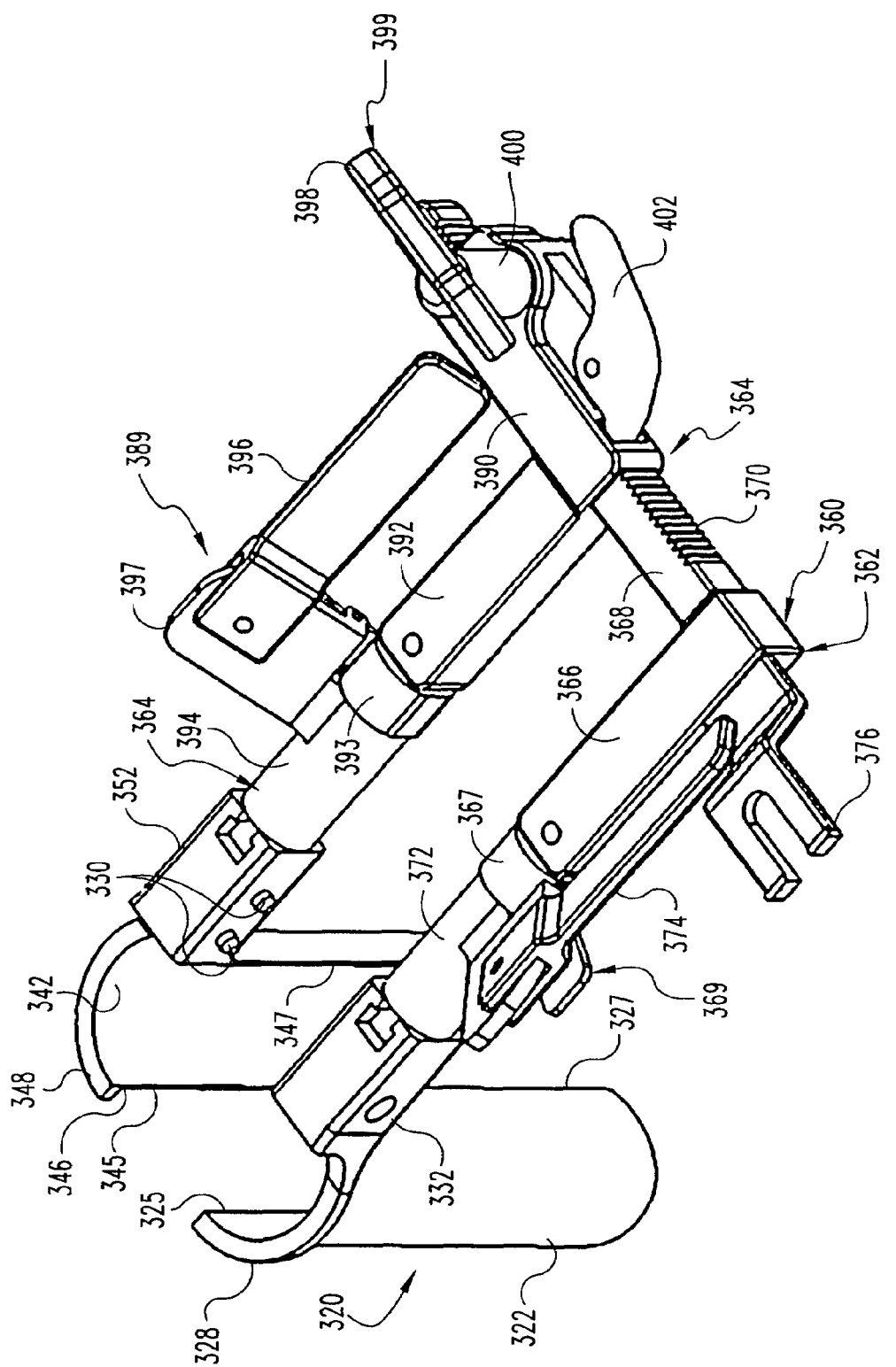
FIG. 19 is another perspective view of the assembly of FIG. 17 with the retractor portions separated.
Figure 20:
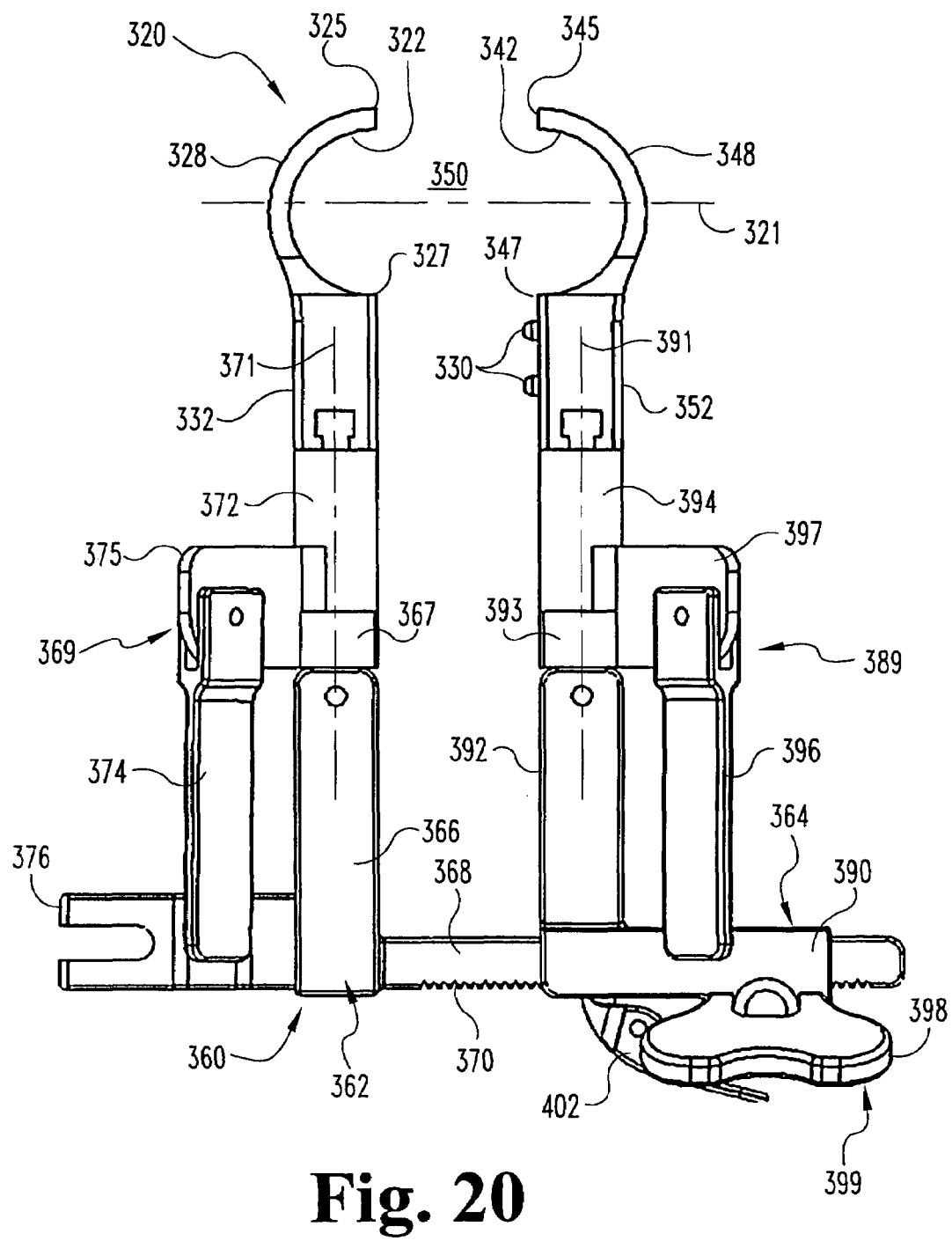
FIG. 20 is a plan view of the assembly of FIG. 19.

As shown in FIGS. 19 and 20, alignment members 330 can be provided along one side of one of the engagement members 332, 352 (engagement member 352 in the illustrated embodiment.) In the illustrated embodiment, alignment members 330 are rounded protrusions which are received in holes provided in the adjacent side of the other engagement member 332, 352 when engagement members 332, 352 are positioned adjacent one another. Alignment members 330 maintain first portion 322 and second portion 342 in longitudinal alignment with one another during and after insertion. Other embodiments contemplate other arrangements for aligning and/or releasably coupling first portion 322 and second portion 342 to one another. Examples of such arrangements include dovetail connections, fasteners, threaded coupling members, clamping members, snap rings, compression bands, straps, ball-detent mechanisms, and releasably interlocking cams or tabs, for example.

Referring to FIGS. 17-20, there is shown a separation instrument 360 operable to move first and second portions 322, 342 away from one another to enlarge working channel 350. It is contemplated that separation instrument 360 includes a lateral separator operable to linearly move first and second retractor portions away from one another along axis 321. It is further contemplated that separation instrument 360 includes at least one rotational separator to pivotally move distal ends of first and second portions 322, 342 away from one another along axis 321. The lateral and rotational separators can be selectively employed by the surgeon during the surgical procedure to enlarge working channel 350 and provide the tissue retraction desired for conducting the surgical procedure through working channel 350. Enlargement of working channel 350 can further retract tissue away from the surgical site distal of the distal ends of retractor portions 322, 342 to provide greater access to tissue, bony structures, and other anatomical spaces located distally of retractor 320.

Separation instrument 360 includes a first connection assembly 362 movably coupled with a second connection assembly 364. First connection assembly 362 is further coupled to first portion 322, and second connection assembly 364 is coupled to second portion 342. First and second connection assemblies 362, 264 extend away from first and second portions 322, 342 and away from the proximal end opening of working channel 350 to facilitate access to working channel 350 during the surgical procedure. First and second connection assemblies 362, 364 are operable to move first and second portions 322, 342 toward and away from one another to separate tissue. First and second connection assemblies 362, 364 further include lever assemblies 369, 389, respectively, that are operable to rotate first and second portions 322, 342 about their proximal ends to move their distal ends away from one another.

Figure 17:
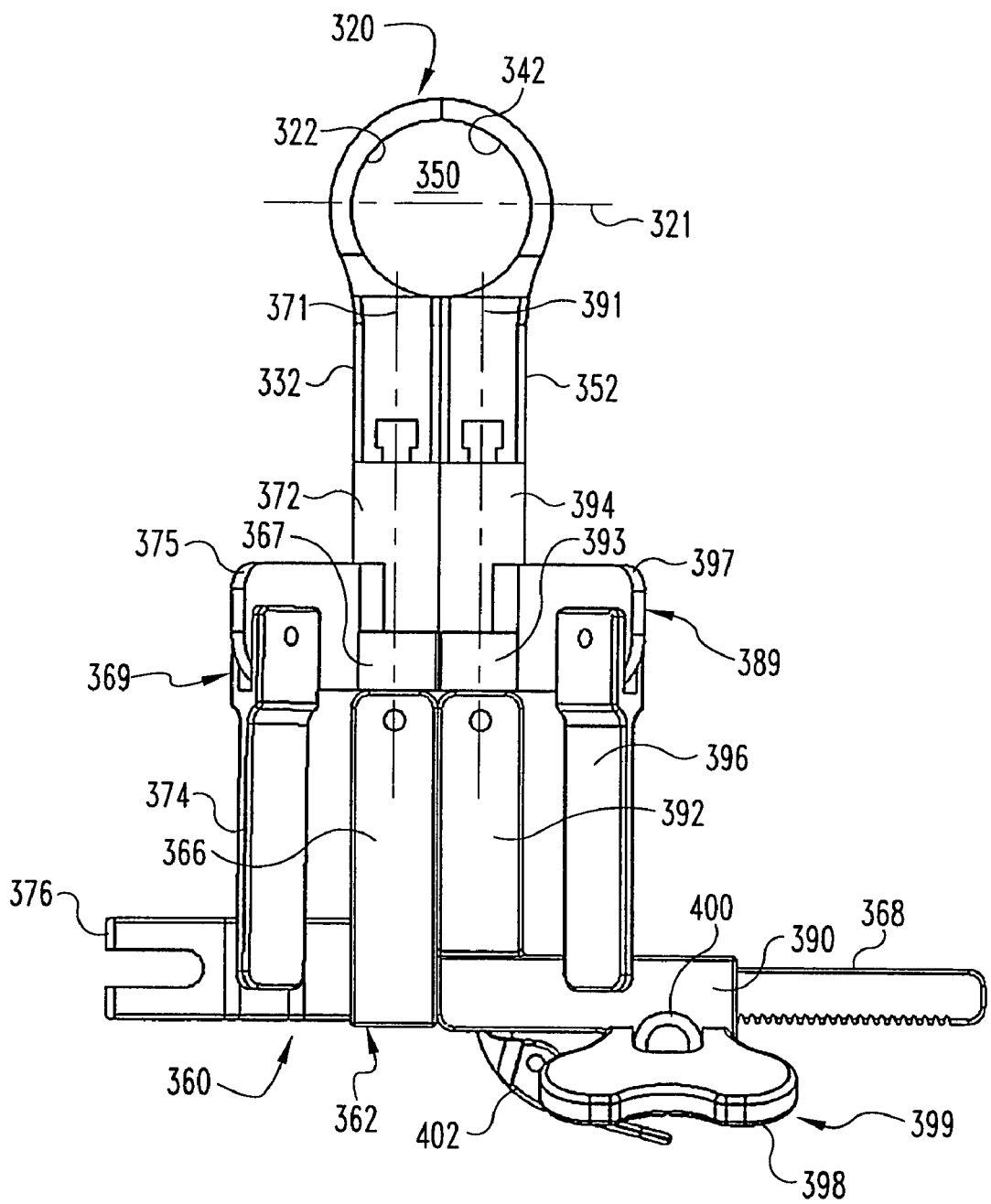
FIG. 17 is a plan view of the retractor of FIG. 15 with a separation instrument engaged thereto.
Figure 18:
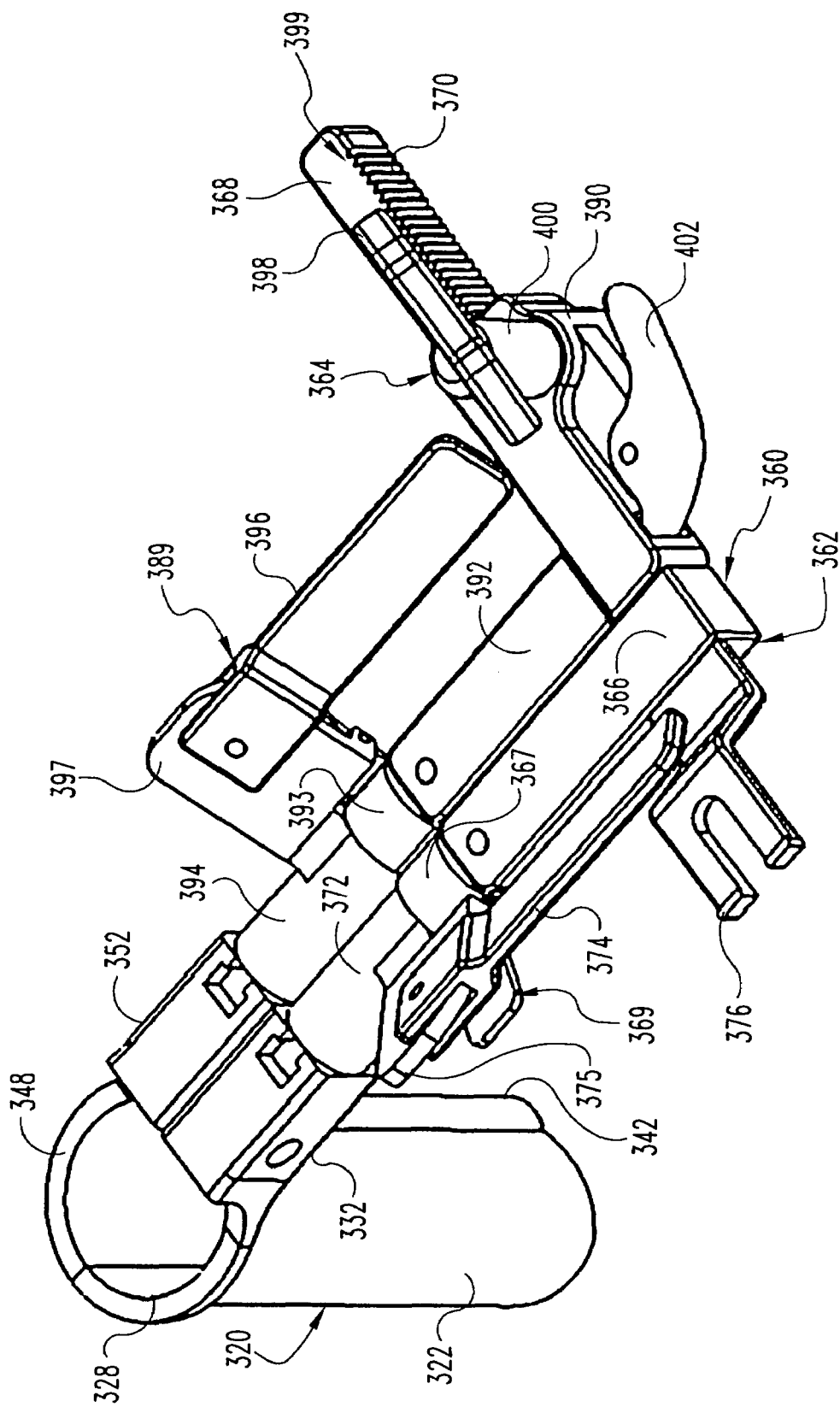
FIG. 18 is a perspective view of the assembly of FIG. 17.
Figure 21:
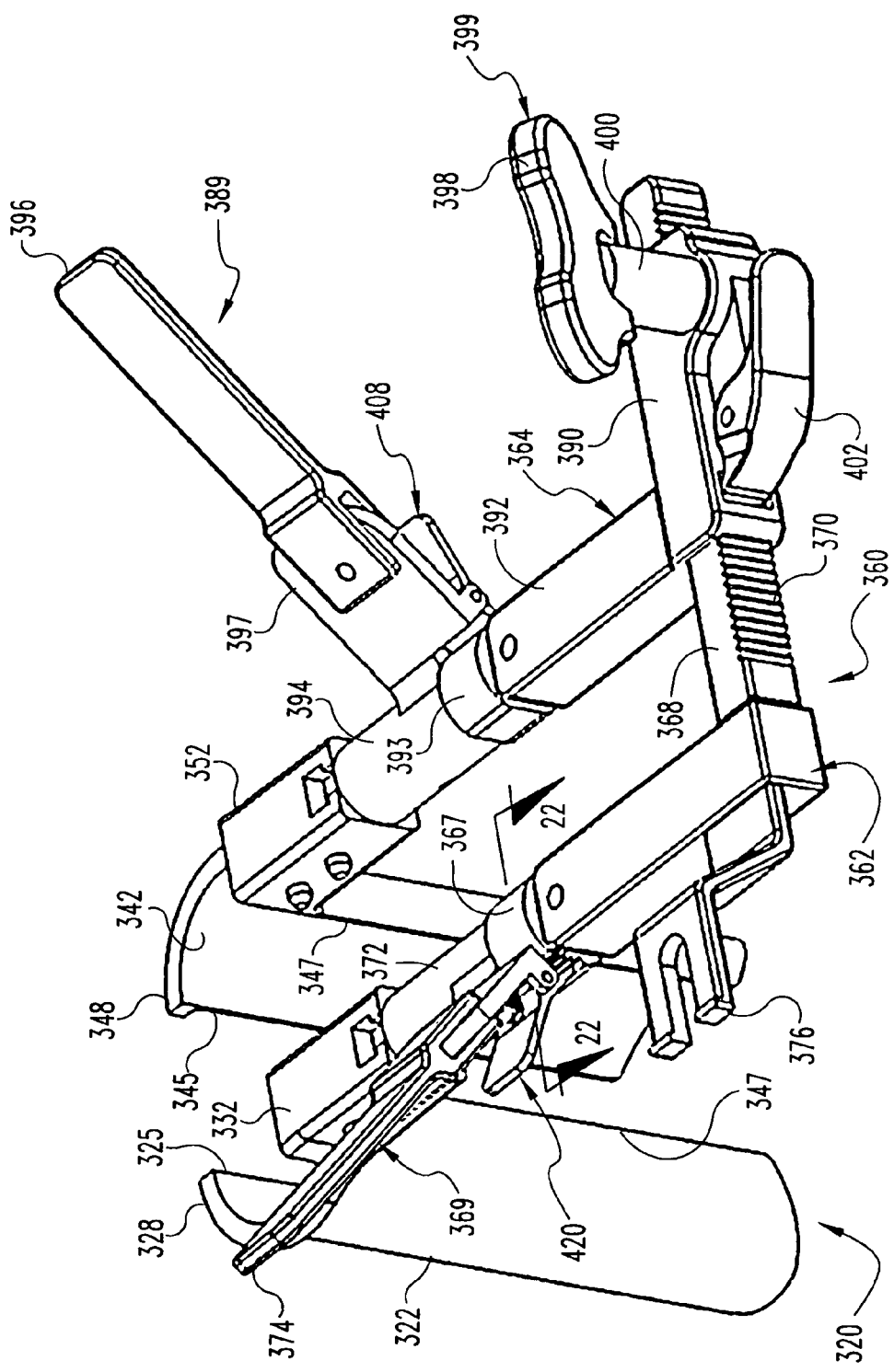
FIG. 21 is a perspective view of the assembly of FIG. 19 with lever arms moved to a pivoting position.
Figure 22:
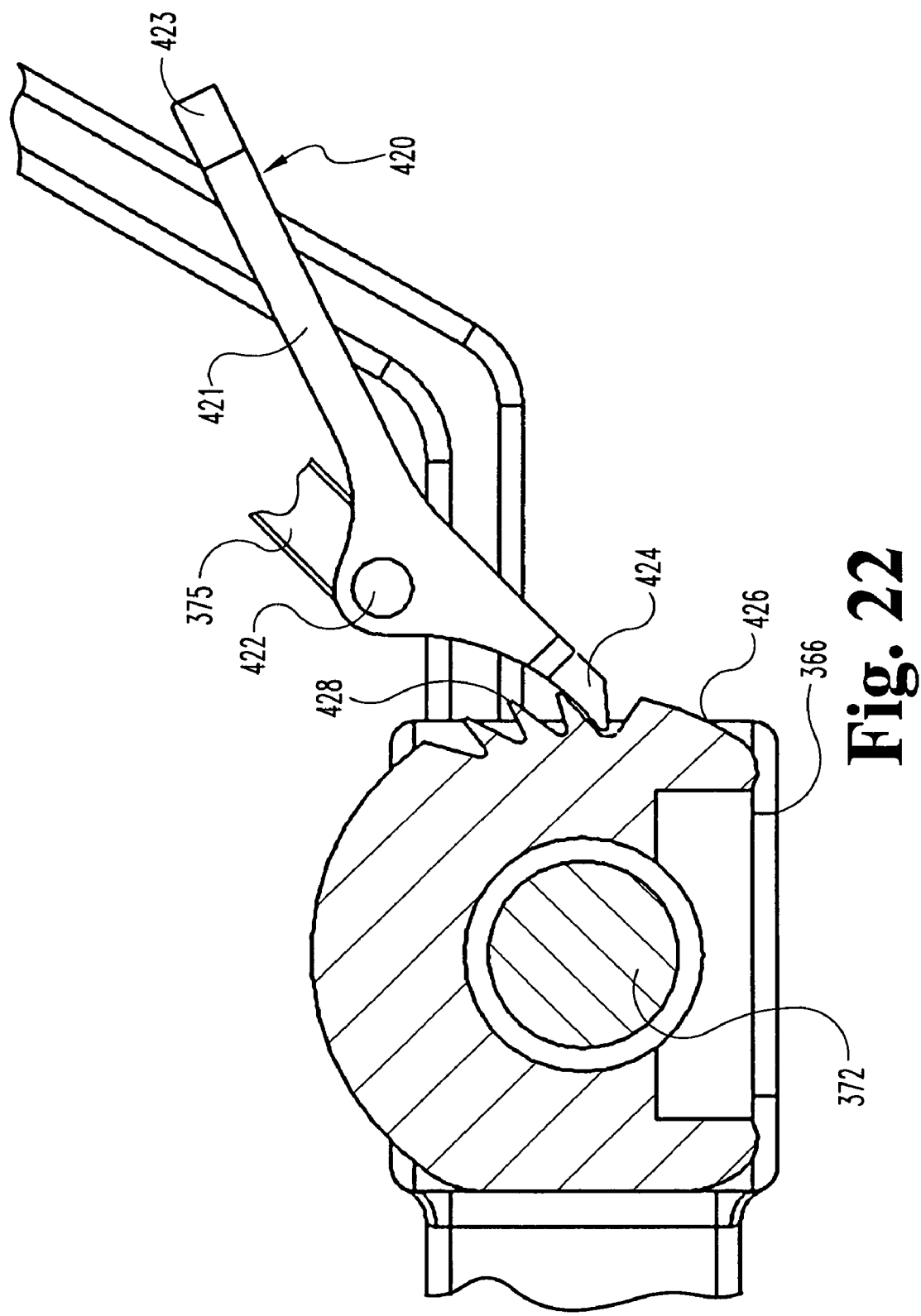
FIG. 22 is a sectional view of a portion of the separation instrument through line 22-22 of FIG. 21 showing a lever arm locking assembly when the retractor portion engaged thereto is in a non-pivoted position.

First connection assembly 362 includes a first engagement arm 372 coupled to first engagement member 332 of first portion 322 and a first extension arm 366 extending from first engagement arm 372. A coupling arm 368 is transversely oriented to and extends from the end of first extension arm 366 opposite first engagement arm 372. A bracket member 376 extends from coupling arm 368, and is engageable by a flexible arm mounted to a surgical table, for example. First connection assembly 362 further includes a first intermediate member 367 fixedly coupled to first extension arm 366. First engagement arm 372 is rotatable relative to intermediate member 367. A first mounting member 375 extends from first engagement arm 372. A first lever arm 374 is pivotally mounted to first mounting member 375 and is movable between a locking position, such as shown in FIG. 17, to a pivoting position, as shown FIG. 21.

Similarly, second connection assembly 364 includes a second engagement arm 394 coupled to second engagement member 352 of second portion 342 and a second extension arm 392 extending from second engagement arm 394. A housing 390 extends from the end of second extension arm 392 opposite second engagement arm 394. Housing 390 includes a passage through which coupling arm 368 is movably received. An adjustment mechanism 399 mounted to housing 390 is engageable to coupling arm 368 and operable to translate coupling arm 368 in housing 390 to effect movement of first and second portions 322, 342 toward and away from one another along translation axis 321.

In the illustrated embodiment, coupling arm 368 includes a number of ratchet teeth 370 formed therealong, which are engageable by adjustment mechanism 399. Adjustment mechanism 399 includes a gear wheel 400 with teeth that interdigitate with teeth 370 to effect movement of coupling arm 368 in housing 390 as handle 398 is rotated. A locking mechanism 402 is spring-biased into engagement with teeth 370, and maintains separation of first and second portions 322, 342 when handle 398 is released. Locking mechanism 402 can also be depressed to pivot its engagement end out of engagement with teeth 470 and allow first and second portions 322, 342 to move toward one another.

Second connection assembly 364 further includes a second intermediate member 393 fixedly coupled to second extension arm 392. Second engagement arm 394 is rotatable relative to intermediate member 393. A second mounting member 397 extends from second engagement arm 394 alongside second intermediate member 393. Second lever arm 396 is pivotally mounted to second mounting member 397 and is movable between a locking position, such as shown in FIG. 17, to a pivoting position, as shown FIG. 21. Intermediate members 367, 393 can be provided as separate components, or can be integral with the respective extension arm.

Figure 23:
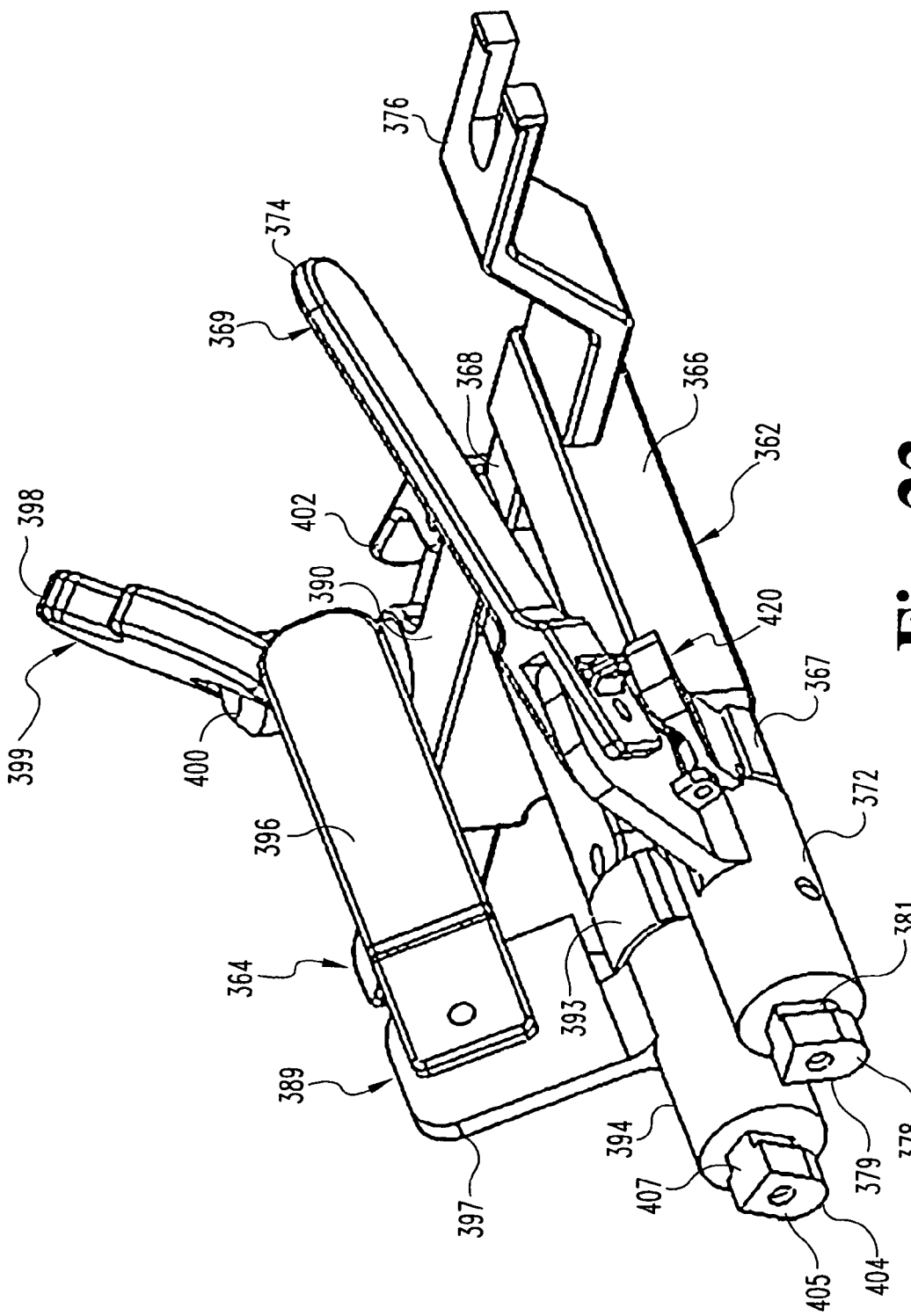
FIG. 23 is perspective view of the separation instrument of FIG. 17 detached from the retractor.
Figure 24:
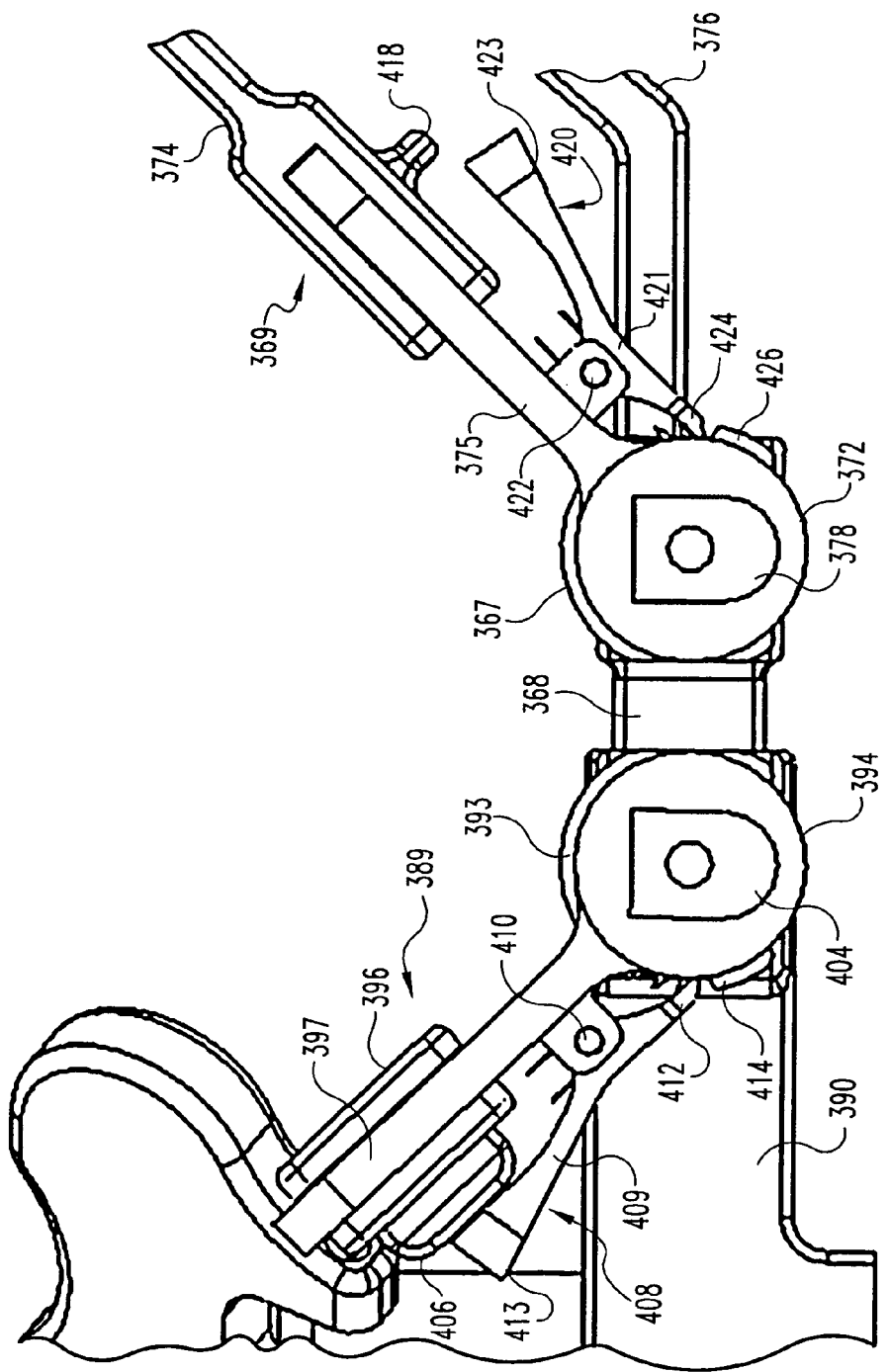
FIG. 24 is an elevation view of a portion of the separation instrument of FIG. 17.
Figure 25:
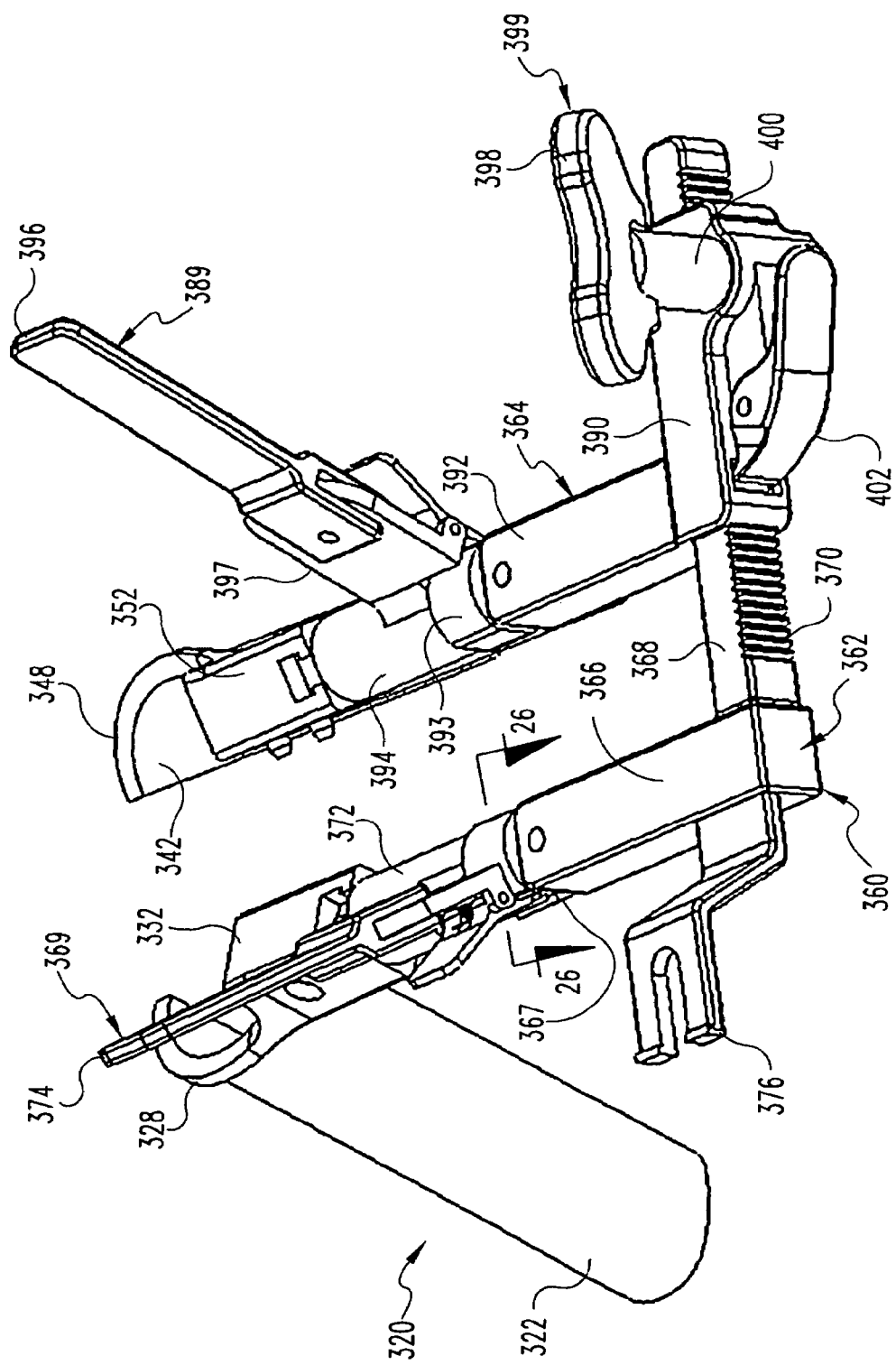
FIG. 25 is a perspective view of the assembly showing the retractor portions pivoted.

As shown in FIGS. 23-24, first and second engagement arms 372, 394 include feet 378, 404, respectively. Feet 378, 404 are slidably and removably received in respective ones of the recesses 333, 353 of engagement members 332, 352. In the illustrated embodiment, feet 378, 404 include an enlarged outer end portion 379, 405 and a smaller cross-section intermediate transition portion 381, 407 extending between engagement arms 372, 394 and the enlarged outer end portion 379, 405. Intermediate transition portions 381, 407 are received in the intermediate keyway openings 335, 355, and enlarged outer end portions 379, 405 are received in receptacles 337, 357.

Feet 378, 404 are received recesses 333, 353 in such a manner that, as discussed further below, lever arms 374, 396 can effect pivoting of first and second retractor portions 322, 342 by rotating engagement arms 372, 394 about their respective axes 371, 391, respectively. Furthermore, separation instrument 360 can be easily removed from first and second retractor portions 322, 342, facilitating clean-up of the instrument assembly after the surgical procedure. It is also contemplated that disposable first and second portions 322, 342 may be used, or that a set of first and second portions 322, 342 can be provided in various lengths, shapes and/or sizes from which a surgeon may select and employ with separation instrument 360.

Figure 26:
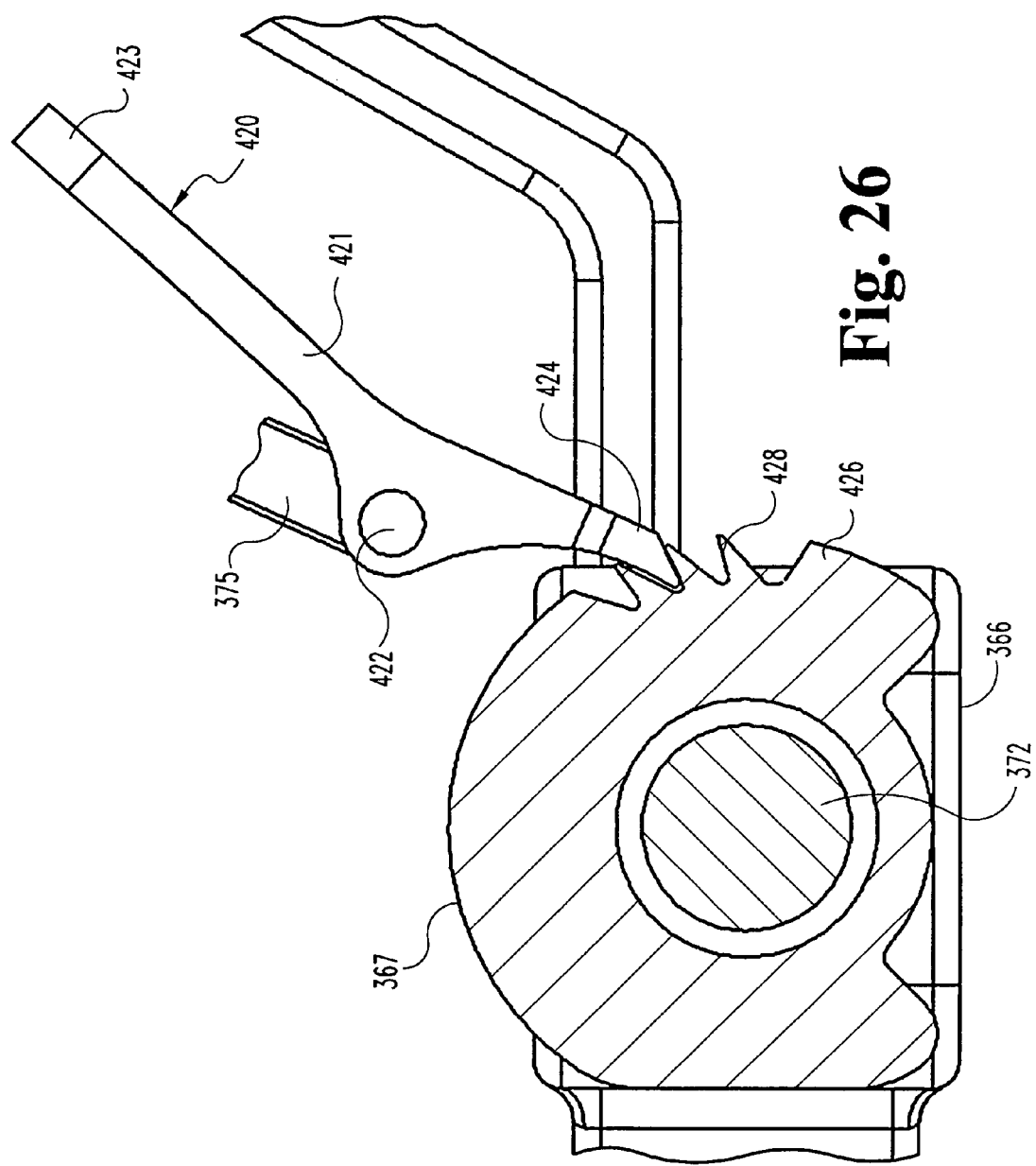
FIG. 26 is a sectional view through line 26-26 of FIG. 25 of a portion of the separation instrument showing the lever arm locking assembly when the retractor portion engaged thereto is in a non-pivoted position.

Intermediate members 367, 393 each include a locking portion, such as engagement portions 426, 414 shown in FIGS. 24, 26, that is engageable with a respective one of the lever arm locking assemblies 420, 408. Lever arm locking assemblies 420, 408 each include a pawl 409, 421 pivotally coupled to an adjacent one of the mounting members 375, 397. For example, as shown in FIGS. 24 and 26, lever arm locking assembly 420 includes a pivot pin 422 mounted to mounting member 375 about which pawl 421 can be pivoted. Similarly, lever arm locking assembly 408 includes a pivot pin 410 mounted to mounting member 397 about which pawl 409 can be pivoted. Intermediate members 367, 393 each include respective ones of engagement portions 426, 414 to which the locking members 420, 408 are engageable to maintain a pivoted position of first and second portions 322, 342.

For example, as shown in FIG. 26 relative to intermediate member 367, there is provided an engagement portion 426 along intermediate member 367 oriented toward pawl 421. Pawl 421 includes a proximal handle portion 423 and a distal engagement end 424. Distal engagement end 424 is positionable in at least one the recesses provided between teeth 428 to maintain a pivoted position of first portion 322. As lever arm 374 is rotated counterclockwise to pivot the distal end of retractor portion 322 away from the distal end of retractor portion 342, pawl 421 moves about engagement portion 426 for engagement there with at a location corresponding to the position of the pivoted retractor portion 322.

Other embodiments contemplate that intermediate members 367, 393 are movable as the respective retractor portion is pivoted. In such embodiments, the pawl 409, 421 does not move or rotate with rotation of engagement arm, but rather remains fixed for engagement with the adjacent engagement portion of the respective intermediate member 367, 393 as it is rotated.

In FIG. 24, first lever arm 374 is shown pivoted on mounting member 375 to its pivoting position, and second lever arm 396 is shown pivoted on mounting member 397 to its locking position. In the locking position, lever arm 396 includes a protrusion 406 that is engageable to the proximal handle portion of pawl 409. In the engaged position, proximal handle portion 413 cannot be moved toward mounting member 397 to remove its engagement end 412 from the teeth along engagement portion 414 of intermediate member 393. Accordingly, the pivoted position of second retractor portion 342 is locked by the positioning of lever arm 396 in its locking position, and second retractor portion 342 cannot be moved unless lever arm 396 is moved to its pivoting position.

In FIG. 24 first lever arm 374 is shown in its pivoting position, and includes a protrusion 418 extending from first lever arm 374 that is positioned out of contact with pawl 421. In this position, pawl 421 can be pivoted about pin 422 to remove engagement end 424 from between teeth 428. Lever arm 374 can then be manipulated to pivot first retractor portion 322 to a desired angular position along axis 321. As lever arm 374 is pivoted, locking member 420 is moved therewith into alignment with another space between teeth 428. When the desired orientation of first portion 322 is obtained, then proximal handle portion 423 can be released, and locking member 420 can be spring biased or otherwise moved to engage engagement portion 426 and maintain the pivoted position of first portion 322. Lever arm 396 can then be pivoted on mounting member 375 to its locking position where protrusion 418 engages pawl 421 to prevent it from being released from engagement portion 426.

Figure 27:
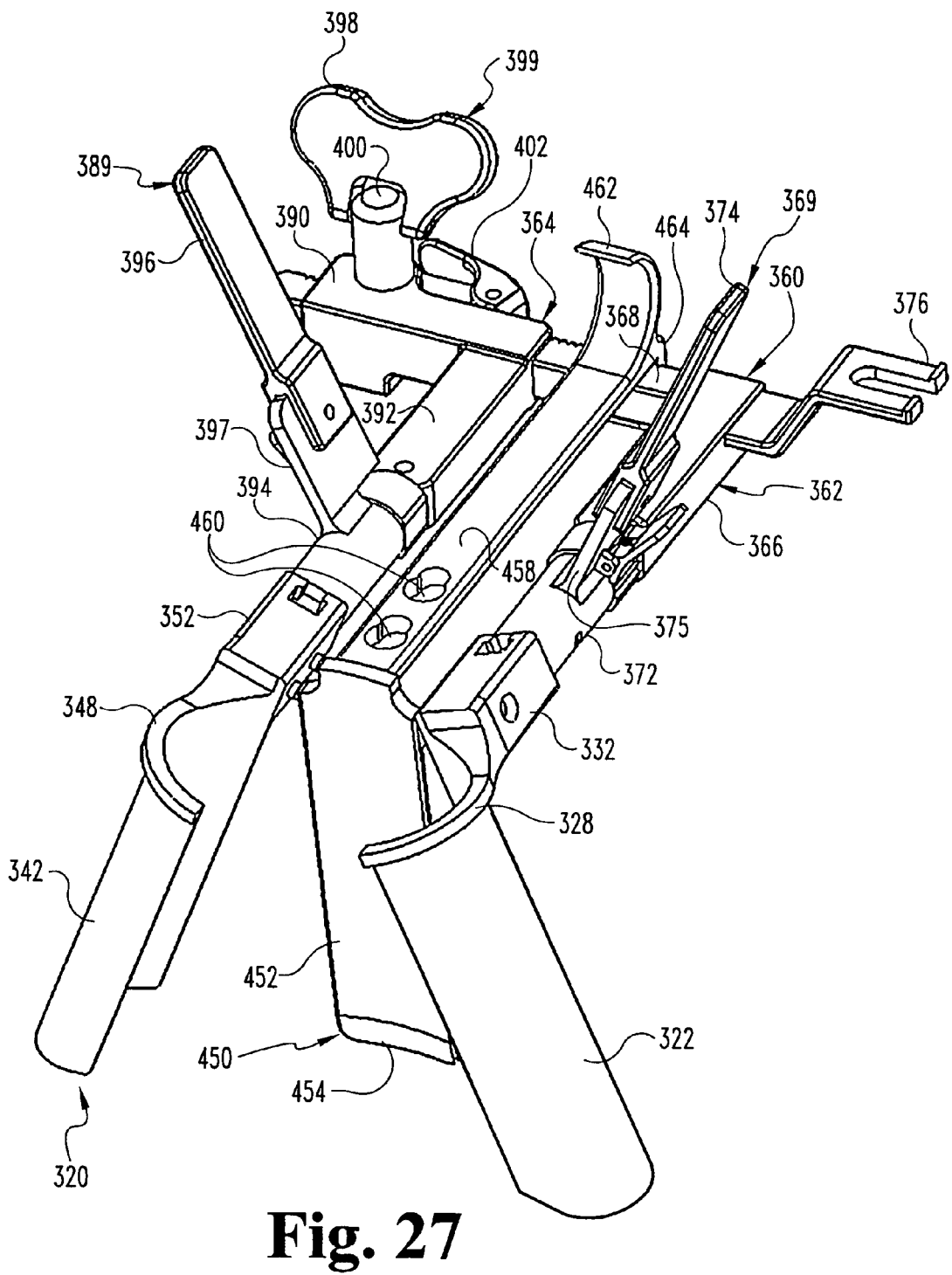
FIG. 27 is a perspective view of the assembly of FIG. 19 showing the retractor portions pivoted and a first intermediate retractor assembly engaged to the separation instrument.
Figure 28:
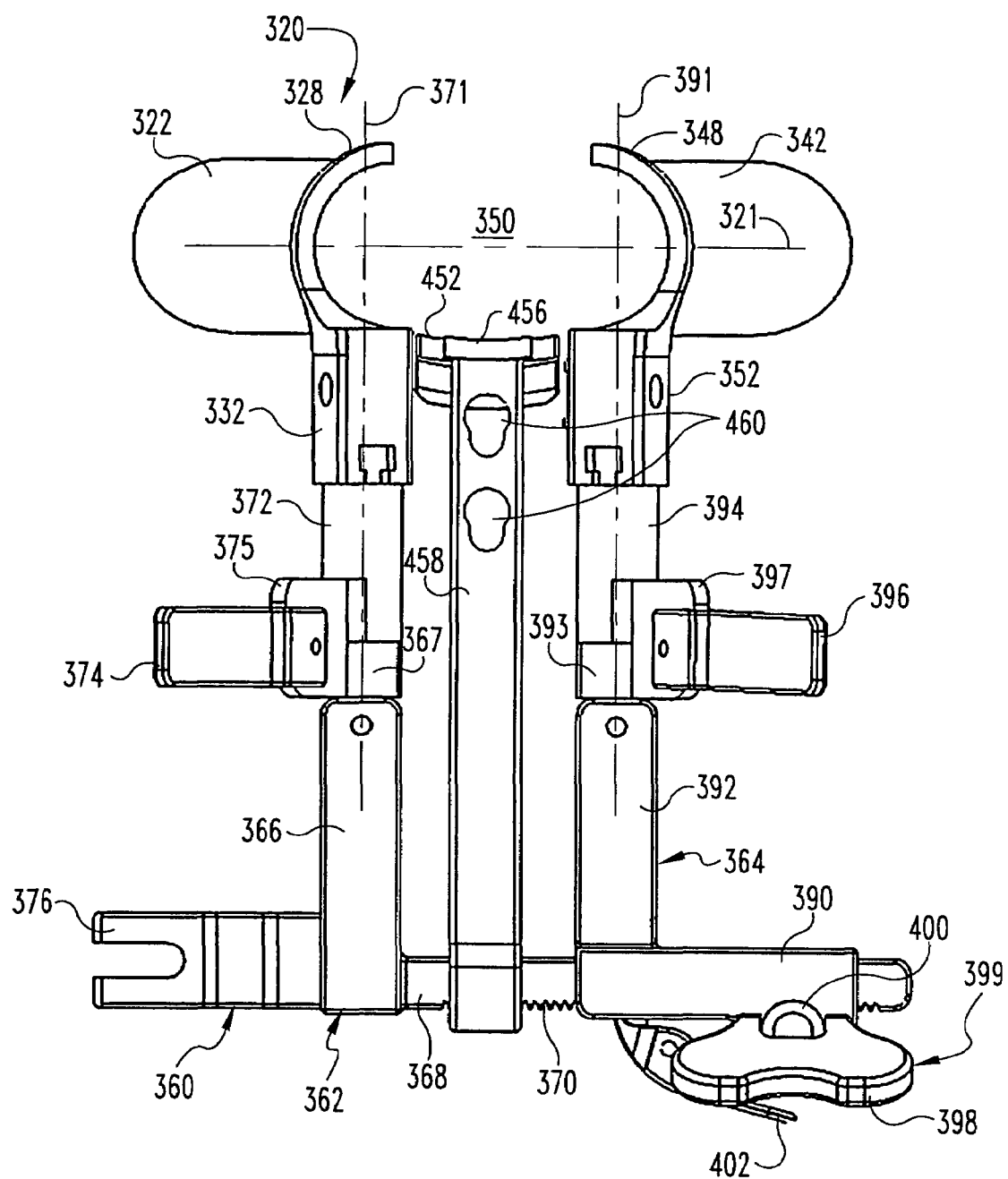
FIG. 28 is a plan view of the assembly of FIG. 27.

Referring to FIGS. 27-28, there is shown a first intermediate retractor assembly 450 engageable to separation instrument 360. Intermediate retractor assembly 450 includes a retractor blade 452 positionable between first and second retractor portions 322, 342 to retract and/or maintain tissue from the working channel 350 in a direction transverse to axis 321. In one operative approach to the spine, retractor 320 is oriented so that retractor portions 322, 342 are movable along axis 321 oriented in the direction of the central axis of the spinal column, and blade 450 is positioned medially or adjacent to the spinal column relative to the other retractor blade portions 322, 342. Other operative orientations in the incisions for the retractor blades and retractor portions are also contemplated.

First intermediate retractor assembly 450 includes blade 452 extending between a distal end 454 and a proximal end 456. As shown in FIG. 28, distal end 454 is curved away from the working channel 350, and can rest upon bone or other tissue when positioned in the retracted incision. Blade 452 can include a flat profile between distal end 454 and proximal end 456, or include a convex curvature about its longitudinal axis or along its longitudinal axis. Blade 452 can also be provided as a single member, or in one or more components movable relative to one another to lengthen or shorten blade 452.

A linking arm 458 is transversely oriented to and extends from proximal end 456 of blade 452. Opposite blade 452 there is provided an engaging portion in the form of first and second hook members 462, 464. Lower hook member 464 can be positioned about coupling arm 368 of separation instrument 360. Linking arm 458 has a length such that the pressure from the tissue at the incision against blade 452 firmly holds hook member 464 against coupling arm 368. Upper hook member 462 can serve as a handle to facilitate placement of lower hook member over coupling arm 368 or removal of intermediate retractor assembly 450. Other arrangements for securing blade 452 to coupling arm 368 are also contemplated, such as fasteners and interfitting components, for example.

Figure 29:
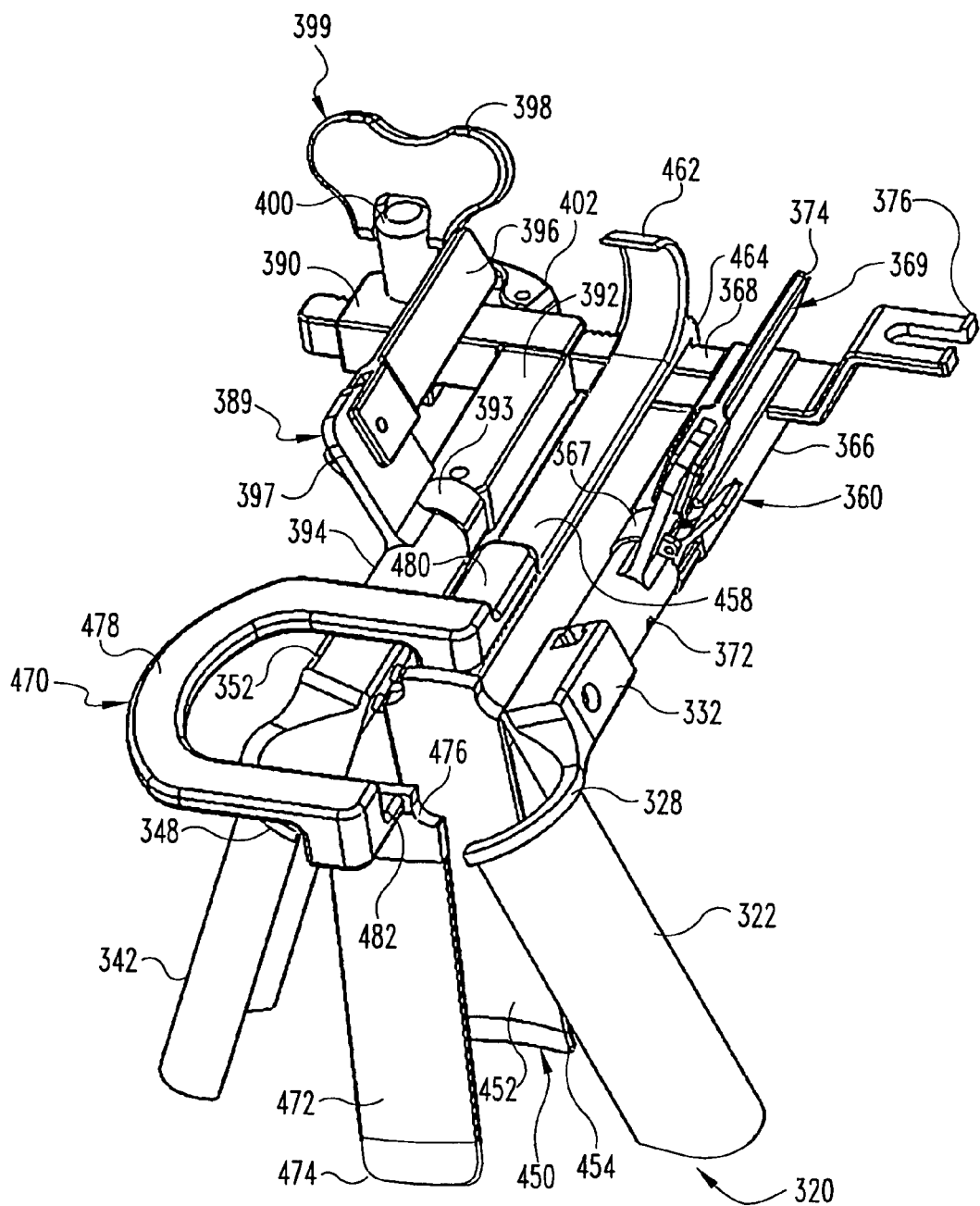
FIG. 29 is a perspective view of the assembly of FIG. 27 with a second intermediate retractor assembly engaged to the first intermediate retractor assembly.
Figure 30:
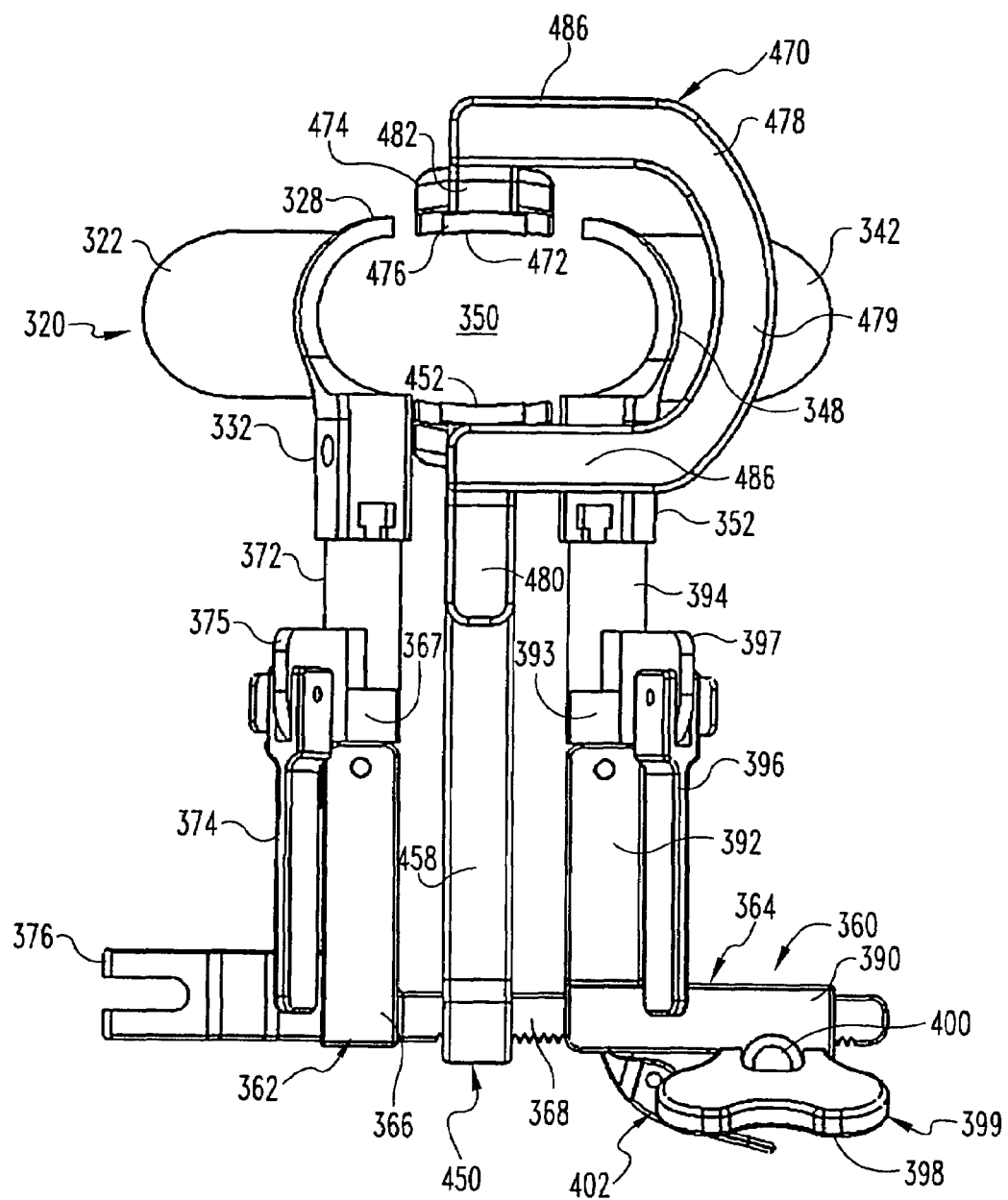
FIG. 30 is a plan view of the assembly of FIG. 30.

First intermediate retractor assembly 450 is further mountable by a second intermediate retractor assembly 470, as shown in FIGS. 29 and 30. Second intermediate retractor assembly 470 includes a blade 472 extending between a distal end 474 and a proximal end 476. Distal end 474 and the blade portion extending therefrom can be configured as discussed above with respect to blade 452. A second linking arm 478 extends from proximal end 476, and includes an engagement foot 480 opposite blade 472. Engagement foot 480 is removably mountable to linking arm 458 of first intermediate retractor assembly 450.

First linking arm 458 includes slotted holes 460 (FIGS. 27-28) extending therethrough adapted to receive pins (not shown) extending from a lower surface of foot 480 of second linking arm 478. The pins can be provided with enlarged heads positionable in the enlarged portions of slotted holes 460, and are slidable to the narrowed ends of the slotted holes 460 so that the heads are captured in slotted holes 460. In the illustrated embodiment, the narrowed portions of the slotted holes 460 extend opposite retractor blade 472 so that the pressure from the tissue about the incision pushing against blade 472 maintains the pins of foot 480 in the narrowed end portions of slotted holes 460.

Second linking arm 478 includes offset portions 486 extending transversely to first linking arm 458. Offset portions 486 are linked by an offset member 479 extending therebetween. Offset member 479 can be provided with an arcuate profile to extend around the respective adjacent retractor portion 322, 342 so as to not obstruct access to working channel 350. Retractor blade 472 can maintain tissue retraction and provide protection to tissue located along the side of the working channel opposite retractor blade 452. First and second intermediate retractor assemblies 450, 470 provide the surgeon with additional options during the surgical procedure with regard to tissue retraction and protection that can be readily employed with separation instrument 360 engaged to retractor 320.

In one surgical procedure, retractor 320 is engaged to separation instrument 360 and inserted in an incision. Retractor 320 can be advanced over one or more dilators dilating an incision, or directly into the incision. Separation instrument 360 is then operated to linearly move retractor portions 322, 342 away from one another along axis 321 to enlarge working channel 350. One or both of the lever arms 374, 396 can be moved to its pivoting position and manipulated to pivot the respective retractor portion 322, 342. When the retractor portion has been pivoted, the respective lever arms are moved to their locking position so that the protrusion extending therefrom engages the adjacent pawl 409, 421 to maintain the pawl in engagement with adjacent engagement portion 414, 426.

When the desired separation has been obtained, the surgeon has the option to select first intermediate retractor assembly 450. Blade 452 is positioned in the incision between the separated first and second retractor portions 322, 342, and linking arm 458 is secured to coupling arm 368. The surgeon has the further option of selecting second intermediate retractor assembly 470, and positioning blade 472 in the incision opposite blade 452. Linking arm 478 can then be secured to linking arm 458. Further adjustment of the spacing and orientation of retractor portions 322, 342 can be completed with separation instrument 360 and/or lever arms 374, 396.

It is further contemplated that retractor portions 322, 342 need not be separated from one another linearly, but are separated during the surgical procedure only by pivoting one or both of them along axis 321. Once the working channel 350 provides the desired access, the surgeon can remove bone, tissue, disc material, or other matter through retractor 320. Implants, such as fusion devices, screws, plates, rods, artificial discs, bone growth material, and other repair devices or therapeutic substances can be delivered through retractor 320 to the desired site in the patient's body.

While the invention has been illustrated and described in detail in the drawings and foregoing description, the same is to be considered as illustrative and not restrictive in character, and that all changes and modifications that come within the spirit of the invention are desired to be protected.

What is claimed is:

1. A retractor assembly for percutaneous surgery in a patient, comprising:
    a first retractor portion having a proximal end and a distal end and being positionable in an incision;
    a second retractor portion having a proximal end and a distal end and being positionable in the incision opposite said first retractor portion, said first and second retractor portions defining an axis extending therebetween;
    a separation instrument coupled between said proximal ends of said first and second retractor portions and being offset to one side of said axis, said separation instrument being operable to move said first and second retractor portions along said axis from an insertion configuration wherein said first and second retractor portions are adjacent one another to a second configuration wherein said first and second portions are separated from one another; and
    an intermediate retractor assembly removably mountable to said separation instrument, said intermediate retractor assembly including a linking arm extending from said separation instrument toward said first and second retractor portions to a retractor blade, said retractor blade being transversely oriented to said linking arm and being positionable in the incision between said first and second retractor portions wherein:
        said first retractor portion and said second retractor portion each includes an engagement member extending laterally therefrom for engagement by said separation instrument;
        one of said engagement members of said first retractor portion and said retractor second portion includes at least one alignment member extending toward said engagement member of the other of said first retractor portion and said second retractor portion; and
        said engagement member of the other of said first retractor portion and said second retractor portion includes at least one receptacle for receiving said at least one alignment member.

2. The assembly of claim 1, wherein said separation instrument includes a first connection assembly connected to said first retractor portion and a second connection assembly connected to said second retractor portion, said first and second connection assemblies being movably coupled with one another.

3. The assembly of claim 2, wherein said first connection assembly includes a first engagement arm engaged to said first retractor portion and extending transversely to said axis and said second connection assembly includes a second engagement arm engaged to said second retractor portion and extending transversely to said axis.

4. The assembly of claim 3, wherein said first and second retractor portions each include an engagement member extending therefrom engageable by respective ones of said engagement arms.

5. The assembly of claim 4, wherein said first and second engagement members each include a recess for removably receiving a foot extending from an end of said engagement arm engaged thereto.

6. The assembly of claim 5, wherein each of said recesses includes a keyway opening at an end of said respective engagement member to receive a stem extending between said respective engagement arm and said foot, each of said recesses further including an enlarged receptacle in communication with said keyway opening sized and shaped to non-rotatably receive said respective foot therein.

7. The assembly of claim 1, wherein said first retractor portion includes a collar about said proximal end thereof and said second retractor portion includes a collar about said proximal end thereof, each of said collars including a respective one of said engagement members extending laterally therefrom.

8. The assembly of claim 1, wherein said linking arm includes a hook portion that is mounted to said separation instrument when said first and second retractor portions are in said second configuration.

9. The assembly of claim 1, wherein each of said first and second retractor portions includes a semi-cylindrical body.

10. The assembly of claim 1, wherein:
said first retractor portion includes opposite edges extending therealong between said proximal end and said distal end thereof;
said second retractor portion includes opposite edges extending therealong between said proximal end and said distal end thereof;
wherein a working channel between said first and second retractor portions is enclosed when said opposite edges of said first retractor portion are adjacent respective ones of said opposite edges of said second retractor portion; and
wherein when said working channel is enlarged said opposite edges of said first retractor portion are separated from respective ones of said opposite edges of said second retractor portion.

11. The assembly of claim 10, wherein said opposite edges of said first retractor portion abut with an adjacent one of said opposite edges of said second retractor portion when said working channel is substantially enclosed by said first and second retractor portions.

12. A retractor assembly for percutaneous surgery in a patient, comprising:
a first retractor portion having a proximal end and a distal end and being positionable in an incision;
a second retractor portion having a proximal end and a distal end and being positionable in the incision opposite said first retractor portion, said first and second retractor portions defining an axis extending therebetween;
a separation instrument coupled between said proximal ends of said first and second retractor portions and being offset to one side of said axis, said separation instrument being operable to move said first and second retractor portions along said axis from an insertion configuration wherein said first and second retractor portions are adjacent one another to a second configuration wherein said first and second portions are separated from one another;
an intermediate retractor assembly removably mountable to said separation instrument, said intermediate retractor assembly including a linking arm extending from said separation instrument toward said first and second retractor portions to a retractor blade, said retractor blade being transversely oriented to said linking arm and being positionable in the incision between said first and second retractor portions when said linking arm is mounted to said separation instrument and said first and second retractor portions are in said second configuration; and
wherein said separation instrument includes a first connection assembly connected to said first retractor portion and a second connection assembly connected to said second retractor portion, said first and second connection assemblies being movably coupled with one another; and
wherein each of said connection assemblies includes an engagement arm coupled to said respective said retractor portion, an extension arm extending from said engagement arm along a second axis that is transverse to said axis extending between said first and second retractor portions, said engagement arm being rotatable about said second axis and relative to said extension arm to pivot said distal end of said respective retractor portion along said axis while said extension arm remains fixed relative to said second axis.

13. The assembly of claim 12, further comprising a lever arm assembly coupled to each of said engagement arms, said lever arm assemblies each including a lever arm manipulatable to rotate said respective engagement arm about an axis thereof and thereby pivot said distal end of said retractor portion engaged thereto.

14. The assembly of claim 13, further comprising a lever arm locking assembly engaged to each of said lever arm assemblies operable to maintain a rotated position of said engagement arm coupled to said lever arm assembly.

15. The assembly of claim 14, wherein said lever arm locking assemblies each include a pawl pivotally coupled to said respective lever arm assembly, said pawl being engageable with an engagement portion along an adjacent one of said extension arms to maintain said rotated position thereof.

16. The assembly of claim 15, wherein each of said pawls and said lever arms is pivotally coupled to a mounting member extending from said adjacent engagement arm.

17. The assembly of claim 16, wherein each of said lever arms is movable between a pivoting position and a locking position, and in said pivoting position each of said lever arms extends from said mounting member and is manipulatable to rotate said adjacent engagement arm and in said locking position each of said lever arms engages said pawl and locks said pawl in engagement with said engagement portion of said adjacent extension arm.

18. The assembly of claim 17, wherein each of said lever arms includes a protrusion that engages a proximal handle portion of said pawl to bias an opposite engagement end of said pawl in engagement with said engagement portion.

19. The assembly of claim 12, further comprising an intermediate member between each of said engagement arms and said extension arms, each of said engagement arms being rotatable relative to said intermediate member, each of said intermediate members including an engagement portion engageable to maintain a rotated position of said engagement arm relative to said intermediate member.

20. The assembly of claim 12, wherein one of said connection assemblies includes a coupling arm extending transversely to said extension arm thereof, and the other of said connection assemblies includes a housing at an end of said extension arm thereof, said coupling arm being received in said housing and engageable with an adjustment mechanism operable to move said first and second retractor portions along said axis.

21. The assembly of claim 20, wherein said coupling arm includes a number of ratchet teeth extending therealong, and said adjustment mechanism includes a gear wheel engageable with said ratchet teeth and operable to effect movement of said coupling arm in said housing thereby moving said first and second retractor portions along said axis.

22. The assembly of claim 1, wherein:
said separation instrument includes first and second engagement arms extending from respective ones of said first and second retractor portions and a coupling arm extending between said first and second engagement arms; and said linking arm of said intermediate retractor assembly is removably engageable to said coupling arm.

23. A retractor assembly for percutaneous surgery in a patient, comprising:

a first retractor portion having a proximal end and a distal end and being positionable in an incision;

a second retractor portion having a proximal end and a distal end and being positionable in the incision opposite said first retractor portion, said first and second retractor portions defining a first axis extending therebetween;

a separation instrument coupled between said proximal ends of said first and second retractor portions and extending away from said proximal ends to one side of said first axis, said separation instrument being operable to move said first and second retractor portions away from one another along said first axis from an insertion configuration wherein said first and second retractor portions are adjacent one another to a second configuration wherein said first and second portions are separated from one another, said separation instrument including including a first connection assembly with a first engagement arm connected to said proximal end of said first retractor portion along a second axis transverse to said first axis and a second connection assembly movably coupled with said first connection assembly and including a second engagement arm extending from said proximal end of said second retractor portion along a third axis transverse to said first axis, wherein said engagement arms each include a rotatable portion adjacent said respective retractor portion that is rotatable about said respective axis thereof to pivot said respective retractor portion engaged thereto about its proximal end, said engagement arms further each including a second portion extending between said separation instrument and said rotatable portion, wherein said second portion is fixed relative to said respective axis and to said separation instrument when said rotatable portion is rotated; and an intermediate retractor assembly removably mountable to said separation instrument, said intermediate retractor assembly including a linking arm extending from said separation instrument toward said first and second retractor portions to a retractor blade, said retractor blade being transversely oriented to said linking arm and being positionable in the incision between said first and second retractor portions when said linking arm is mounted to said separation instrument and said first and second retractor portions are in said second configuration.

24. The assembly of claim 23, wherein said separation instrument further comprises a coupling arm extending between said engagement arms and an adjustment mechanism engaged to said coupling arm to couple said engagement arms and said retractor portions to one another for linear movement in a direction of said first axis and transversely to said second and third axes.

25. The assembly of claim 23, wherein said first and second retractor portions each include an engagement member extending transversely therefrom, said engagement members being engageable by a respective one of said engagement arms, wherein said engagement members extend along respective ones of said first and second axes when engaged to said respective engagement arm.

26. The assembly of claim 25, wherein said first and second engagement members each include a recess for removably receiving a foot extending from an end of said respective engagement arm.

27. The assembly of claim 23, further comprising a lever arm coupled to said rotatable portion of each of said engagement arms and extending from said rotatable portion at a position between said separation instrument and said respective retractor portion, said lever arms being manipulatable to rotate said rotatable portion about said respective axis of said engagement arm thereby pivoting said retractor portion engaged thereto.

28. The assembly of claim 27, further comprising a lever arm locking assembly on said rotatable portion of each of said engagement arms, said lever arm locking assemblies each being releasably engageable with an engagement portion of said second portion of said engagement arm, wherein said engagement portion is positioned on an end of said second portion opposite said separation instrument.

29. The assembly of claim 28, wherein said lever arm locking assemblies each include a pawl mounted to said rotatable portion of each of said engagement arms, said pawls each being engageable with said engagement portion.

30. The assembly of claim 29, wherein said pawls are each pivotally coupled to a mounting member extending from said rotatable portion of said respective engagement arm.

31. The assembly of claim 30, wherein each of said lever arms is movable between a pivoting position and a locking position, and in said pivoting position said lever arms extend from said respective mounting member and are manipulatable to rotate said rotatable portion of said engagement arm and in said locking position said lever arms each engage said respective pawl and lock said pawl in engagement with said engagement portion.

32. The assembly of claim 31, wherein each of said lever arms includes a protrusion that engages a proximal handle portion of said respective pawl to bias an opposite engagement end of said pawl in engagement with said engagement portion.

33. The assembly of claim 24, wherein said second portion of each of said engagement arms includes an extension arm extending between said coupling arm and said rotatable portion, said extension arm being fixed relative to said rotatable portion.

34. The assembly of claim 33, further comprising an intermediate member between each of said rotatable portions and said extension arms, said intermediate members each including an engagement portion thereon for engagement by a lever arm locking assembly to maintain a pivoted position of said respective retractor portion.

35. The assembly of claim 24, wherein said rotatable portion of each of said engagement arms includes a lever arm mounted thereto, said lever arms each being offset from said proximal end of said respective retractor portion along said axis of said respective engagement arm.

36. A retractor assembly for percutaneous surgery in a patient, comprising:

a first retractor portion having a proximal end and a distal end and being positionable in an incision;

a second retractor portion having a proximal end and a distal end and being positionable in the incision opposite said first retractor portion, said first and second retractor portions defining a first axis extending therebetween;

a separation instrument coupled between said proximal ends of said first and second retractor portions and extending from said proximal ends offset to one side of said axis, said separation instrument being operable to move said first and second retractor portions along said axis from an insertion configuration wherein said first and second retractor portions are adjacent one another to a second configuration wherein said first and second portions are separated from one another, said separation instrument including a first connection assembly with a first engagement arm extending from said proximal end of said first retractor portion and a first extension arm extending from said first engagement arm along a second axis transverse to said first axis and a second connection assembly movably coupled with said first connection assembly, said second connection assembly including a second engagement arm extending from said proximal end of said second retractor portion and a second extension arm extending from said second engagement arm along a third axis transverse to said first axis, wherein said engagement arms are each rotatable relative to said respective extension arm about said respective axis thereof to pivot said distal end of said respective retractor portion along said first axis while said respective extension arm remains fixed relative to said respective axis and a lever arm extending from said respective engagement arm operable to rotate said engagement arm and pivot said respective retractor portion engaged thereto about its proximal end, wherein said lever arm is positioned along said respective engagement arm at a location between said separation instrument and said respective retractor portion; and an intermediate retractor assembly removably mountable to said separation instrument, said intermediate retractor assembly including a linking arm extending from said separation instrument toward said first and second retractor portions to a retractor blade, said retractor blade being transversely oriented to said linking arm and being positionable in the incision between said first and second retractor portions when said linking arm is mounted to said separation instrument and said first and second retractor portions are in said second configuration.

37. The assembly of claim 36, wherein said separation instrument is structured to move said first and second retractor portions linearly away from one another along said first axis.

38. The assembly of claim 37, wherein said separation instrument further comprises a coupling arm extending between said engagement arms and an adjustment mechanism engaged to said coupling arm to couple said engagement arms and said retractor portions to one another for linear movement in a direction of said first axis and transversely to said second and third axes.

39. The assembly of claim 36, further comprising a mounting member extending from each of said first and second engagement arms, wherein each of said lever arms is pivotally mounted to a respective one of said mounting members and extends transversely to said respective axis of said engagement arm in a first position and is pivotal from said first position to a second position extending along said respective axis.

40. The assembly of claim 36, further comprising a lever arm locking assembly mounted to each of said engagement arms operable to maintain a rotated position of said engagement arms.

41. The assembly of claim 40, wherein said lever arm locking assemblies each include a pawl mounted to each of said engagement arms, said pawls each being engageable with an engagement portion along said respective extension arm.

42. The assembly of claim 41, wherein said pawls and said lever arms are each pivotally coupled to a mounting member extending from said respective engagement arm.

43. The assembly of claim 42, wherein each of said lever arms is movable between a pivoting position and a locking position, and in said pivoting position said lever arms extend from said respective mounting member and are manipulatable to rotate said respective engagement arm and in said locking position said lever arms engage said respective pawl and lock said pawl in engagement with said engagement portion.

44. The assembly of claim 43, wherein each of said lever arms includes a protrusion that engages a proximal handle portion of said pawl adjacent thereto to bias an opposite engagement end of said pawl in engagement with said engagement portion.

* * * * *